(12) United States Patent
Yun et al.

(10) Patent No.: US 8,187,865 B2
(45) Date of Patent: May 29, 2012

(54) NANOWIRE SENSOR, SENSOR ARRAY, AND METHOD FOR MAKING THE SAME

(75) Inventors: Minhee Yun, La Crescenta, CA (US);
Nosang Myung, Rosemead, CA (US);
Richard Vasquez, Altadena, CA (US);
Margie Homer, Pasadena, CA (US);
Margaret Ryan, Pasadena, CA (US);
Shiao-Pin Yen, Altadena, CA (US);
Jean-Pierre Fleurial, Altadena, CA (US); Ratnakumar Bugga, Arcadia, CA (US); Daniel Choi, Los Angeles, CA (US); William Goddard, Pasadena, CA (US); Abhijit Shevade, Pasadena, CA (US); Mario Blanco, Temple City, CA (US); Tahir Cagin, Arcadia, CA (US); Wely Floriano, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 307 days.

(21) Appl. No.: 12/455,186

(22) Filed: May 29, 2009

(65) Prior Publication Data
US 2009/0242416 A1    Oct. 1, 2009

Related U.S. Application Data

(62) Division of application No. 10/868,755, filed on Jun. 14, 2004, now abandoned.

(60) Provisional application No. 60/477,838, filed on Jun. 12, 2003, provisional application No. 60/477,841, filed on Jun. 12, 2003.

(51) Int. Cl.
*C12M 1/34* (2006.01)
*C12M 3/00* (2006.01)

(52) U.S. Cl. ............. 435/287.2; 977/762; 422/68.1; 422/82.01; 422/82.02; 435/283.1; 435/287.1; 435/288.3

(58) Field of Classification Search ............... 435/287.2, 435/283.1, 287.1, 288.3; 422/68.1, 82.01, 422/82.02; 977/762
See application file for complete search history.

(56) References Cited

U.S. PATENT DOCUMENTS 5,234,566 A * 8/1993 Osman et al. ............ 204/403.06
(Continued)

OTHER PUBLICATIONS

H. Nanto and J. Stetter, in Handbook of Machine Olfaction, T. Pearce, S. Schifman, H. Nagle and J. Gardner, eds, 2003, Wiley-VCH, 79-104.

(Continued)

*Primary Examiner* — Melanie J Yu
(74) *Attorney, Agent, or Firm* — Tope-McKay & Associates; Autumn Villarreal

(57) ABSTRACT

The present invention relates to a nanowire sensor and method for forming the same. More specifically, the nanowire sensor comprises at least one nanowire formed on a substrate, with a sensor receptor disposed on a surface of the nanowire, thereby forming a receptor-coated nanowire. The nanowire sensor can be arranged as a sensor sub-unit comprising a plurality of homogeneously receptor-coated nanowires. A plurality of sensor subunits can be formed to collectively comprise a nanowire sensor array. Each sensor subunit in the nanowire sensor array can be formed to sense a different stimulus, allowing a user to sense a plurality of stimuli. Additionally, each sensor subunit can be formed to sense the same stimuli through different aspects of the stimulus. The sensor array is fabricated through a variety of techniques, such as by creating nanopores on a substrate and electrodepositing nanowires within the nanopores.

14 Claims, 28 Drawing Sheets

U.S. PATENT DOCUMENTS

| | | | |
|---|---|---|---|
| 6,461,528 | B1* | 10/2002 | Scherer et al. .................. 216/56 |
| 6,831,017 | B1* | 12/2004 | Li et al. .......................... 438/694 |
| 7,163,659 | B2 | 1/2007 | Stasiak et al. |
| 2002/0187504 | A1* | 12/2002 | Reich et al. ....................... 435/6 |
| 2006/0200044 | A1 | 9/2006 | Freeman et al. |
| 2007/0264634 | A1 | 11/2007 | Bock et al. |

OTHER PUBLICATIONS

G. Bidan Sens Actuators B 1992, 6, 45, Electroconducting conjugated polymers: new sensitive matrices to build up chemical or electrochemical sensors.

F. Beck, M. Dalhaus, N. Zahedi, Electrochimica Acta, 1992, 7, 1265, Anodic codeposition of polypyrrole and dispersed TiO2.

B. Das and S. P. McGinnis, Appl. Phys. A 71, 681-688 (2000), Novel template-based semiconductor nanostructures and their applications.

H. Masuda, and K. Fukuda "Ordered Metal Nanohole Arrays Made by a Two-Step Replication of Honeycomb Structures of Anodic Alumina," Science, 268, 1466 (1995).

H. Masuda, F. Hasegwa, and S. Ono, "Self-Ordering of Cell Arrangement of Anodic Porous Alumina Formed in Sulfuric Acid Solution," J. Electrochem. Soc., 144(5), L127-L130, (1997).

D. Routkevitch, A.A. Tager, J. Haruyama, M. Moskovits, and J.M. Xu et al., "Nonlithographic Nanowire Arrays : Fabrication, Physics, and Device Applications" IEEE Transaction on Electron Devices 43 : Special Issue on Present and Future Trends in Device Science and Technologies, pp. 1646-1658 (1996), and references therein.

Handbook of Conducting Polymers, 2nd Edition, T. A. Skotheim, R.L. Elsenbaumer, J.R. Reynolds, eds., 1998, Marcel Dekker.

H. Ding, S.M. Park, J. Electrochem. Soc. 2003, 150, E33, Electrochemistry of conductive polymers.

J. W. Gardner, P.N. Nartlett. "Potential applications of electropolymerized thin organic films in nanotechnology," Nanotechnology, 1991, 2, 19.

C. Z. Li, H. X. He, A. Bogozi, J. S. Bunch, and N. J. Tao, Appl. Phys. Lett. 76, 1333 (2000), Molecular detection based on conductance of quantization of nanowires.

L. Roschier, J. Pentilla, M. Martin, P. Hakonen, M. Paalanen, U. Tapper, E. I. Kauppinen, C. Journet, and P. Bernier, Appl. Phys. Lett. 75, 728 (1999), Single electron transistor made of multiwalled carbon nanotubed using scanning probe manipulation.

P. A. Smith, C. D. Nordquist, T. N. Jackson, T. S. Mayer, B. R. Martin, J. Mbindyo, and T.E. Mallouk, Appl. Phys. Lett. 77, 1399 (2000), Electric field assisted assembly and alignment of metallic nanowires.

N. R. Franklin, Q. Wang, T. W. Tombler, A. Javey, M. Shim, and H. Dai, Appl. Phys. Lett. 81, 913 (2002), Integration of suspended carbon nanotube arrays into electronic devices.

M. A. Guillorn, M. D. Hale, V. I. Merkulov, M. L. Simpson, G. Y. Eres, H. Cui, A. A. Puretzky and D. B. Geohegan, Appl. Phys. Lett. 81, 2860 (2002), Operation of individually integrally gated carbon nanotube field emitter cells.

M. Yun, N. V. Myung, R. P. Vasquez, J. Wang, and H. Monbouquette, "Nanowire Growth for Sensor Arrays", in Nanofabrication Technologies, Ed. E. A. Dobisz, SPIE Proceedings 5220, 37 (2003).

T. Thorsen, S. J. Maerkl, and S. R. Quake, Science 298, 580 (2002), Microfluidic large scale integration.

T. R. I. Cataldi, D. Centonze, and A. Guerrieri, Anal. Chem. 67, 101 (1995), Mixed valent ruthenium oxide ruthenium cyanide inorganic film on glassy carbon electrodes as an amperometric sensor of aliphatic alcohols.

F. Yue, T. S. Ngin, and G. Hailin, Sensors and Actuators B 32, 33 (1996), A novel paper pH sensor based on polypyrrole.

M. G. Buehler, G. M. Kuhlman, N. V. Myung, D. Keymeulen, S. P. Kounaves, D. Newman, and D. Lies, presented at the International Conference on Environmental Systems, Vancouver, Jul. 7-10, 2003 (proceedings in press), Planar array redox cells and pH sensors for ISS water quality and microbe detection.

N. A. Melosh, A. Boukai, F. Diana, B. Gerardot, A. Badolato, P. M. Petroff, and J. R. Heath, Science 300, 112 (2003), Ultrahigh density nanowire lattices and circuits.

A. Ural, Y. Li, and H. Dai, Appl. Phys. Lett. 81, 3464 (2002), Electric field aligned growth of single wall carbon nanotubes on surfaces.

Y. Huang, X. Duan, Y. Cui, L. J. Lauhon, K.-H. Kim, and C. M. Lieber, Science 294, 1313 (2001), Logic gates and computation from assembled nanowire building blocks.

Y. Huang, X. Duan, Q. Wei, and C. M. Lieber, Science 291, 630 (2001), Directed assembly of one-dimensional nanostructures into functional networks.

X. Duan, Y. Huang, Y. Cui, J. Wang, and C. M. Lieber, Nature 409, 66 (2001), Indium phosphide nanowires as building blocks for nanoscale eiectronic and optoelectronic devices.

A. Bachtold, P. Hadley, T. Nakanishi, and C. Dekker, Science 294, 1317 (2001), Logic circuits with carbon nanotube transistors.

A. Bezryadin, A. R. M. Verschueren, S. J. Tans, and C. Dekker, Phys. Rev. Lett. 80, 4036 (1998), Multiprobe transport experiments on individual single wall carbon nanotubes.

S. J. Tans, A. R. M. Verschueren, and C. Dekker, Nature 393, 49 (1998), Room temperatures transistor based on a single carbon nanotube.

A. Star, J.-C. P. Gabriel, K. Bradley, and G. Gruner, Nano Lett. 3, 459 (2003), Electrohic detection of specific protein binding using nanotube FET devices.

F. Favier, E. C. Walter, M. P. Zach, T Benter, and R. M. Penner, Science 293, 2227 (2001), Hydrogen sensors and switches from electrodeposited palladium mesowire arrays.

Y. Cui, Q. Wei, H. Park, and C. M. Lieber, Science 293, 1289 (2001), Nanowire nanosensors for highly sensitive and selective detection of biologicland chemical species.

Bartlett, P. N.; Chung, S. K. L. Sensors and Actuators 1989, 19, 141, Conducting polymer gas sensors, Part II.

Bartlett, P. N. Sensors and Actuators 1989, 19, 125, Conducting polymer gas sensors, Part I.

Josowicz, M. Anal. Chem. 1987, 59, 253, Electrochemical and UV visible spectroelectrochemical investigation of selectivity of potentiomerric gas sensors based on polypyrrole.

Sakai, Y. Sensors and Actuators 1986, 9, 125, Determination of nitrate based on the increase of electrical conductivity of polyacetylene film in acidified nitrate solutions.

J.J. Miasik, A. Hooper, B.C. Tofield; "Conducting polymer gas sensor" J. Chem.Soc., Faraday Trans., 1986, 182, 1117.

Gustaffson, G.; Lundstrom, I. In Proc.2nd Intl. Meeting on Chemical Sensors: 1986, Influence of ammonia based on the physical properties of polypyrrole.

Cao, et al., "Array of nickel nanowires enveloped in polyaniline nanotubules and its magnetic behavior," 2001, Applied Physics Letters, vol. 78, No. 11, pp. 1592-1594.

* cited by examiner

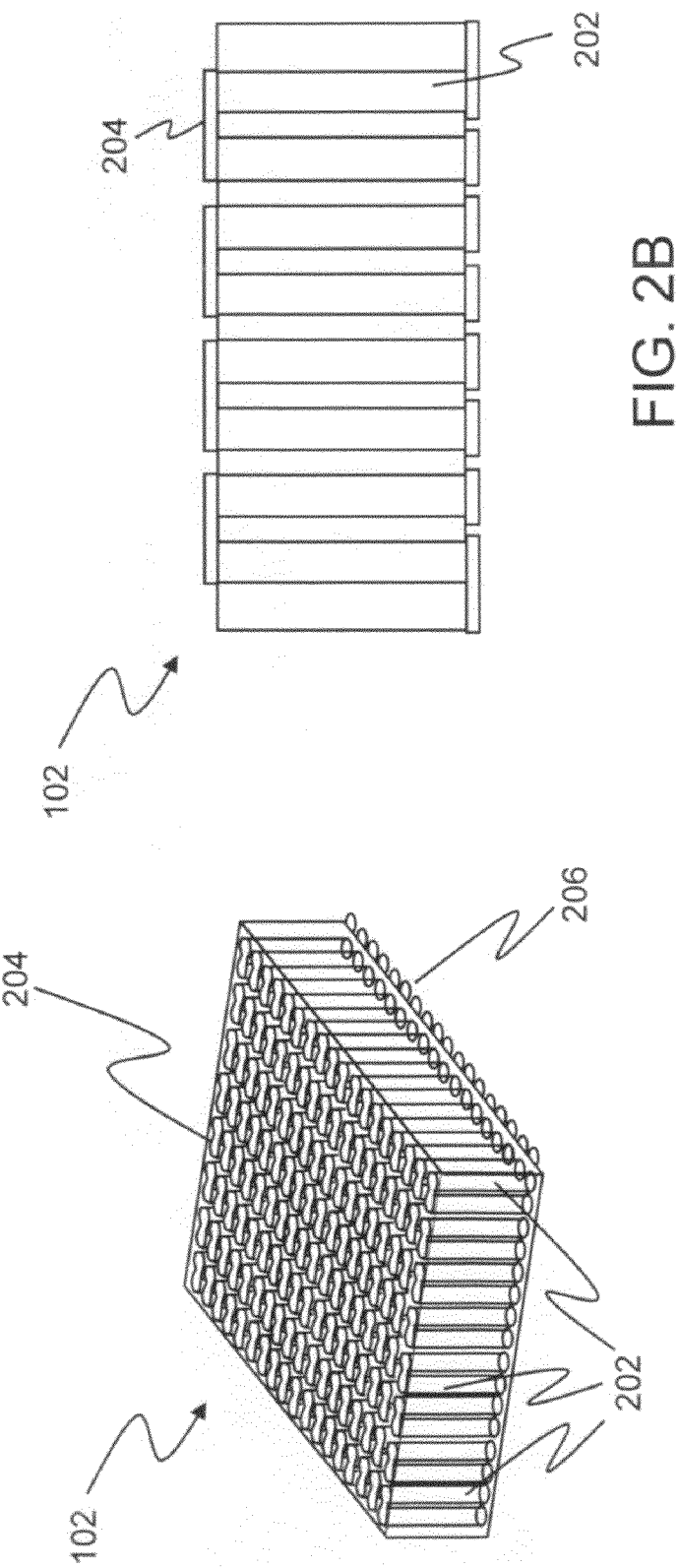

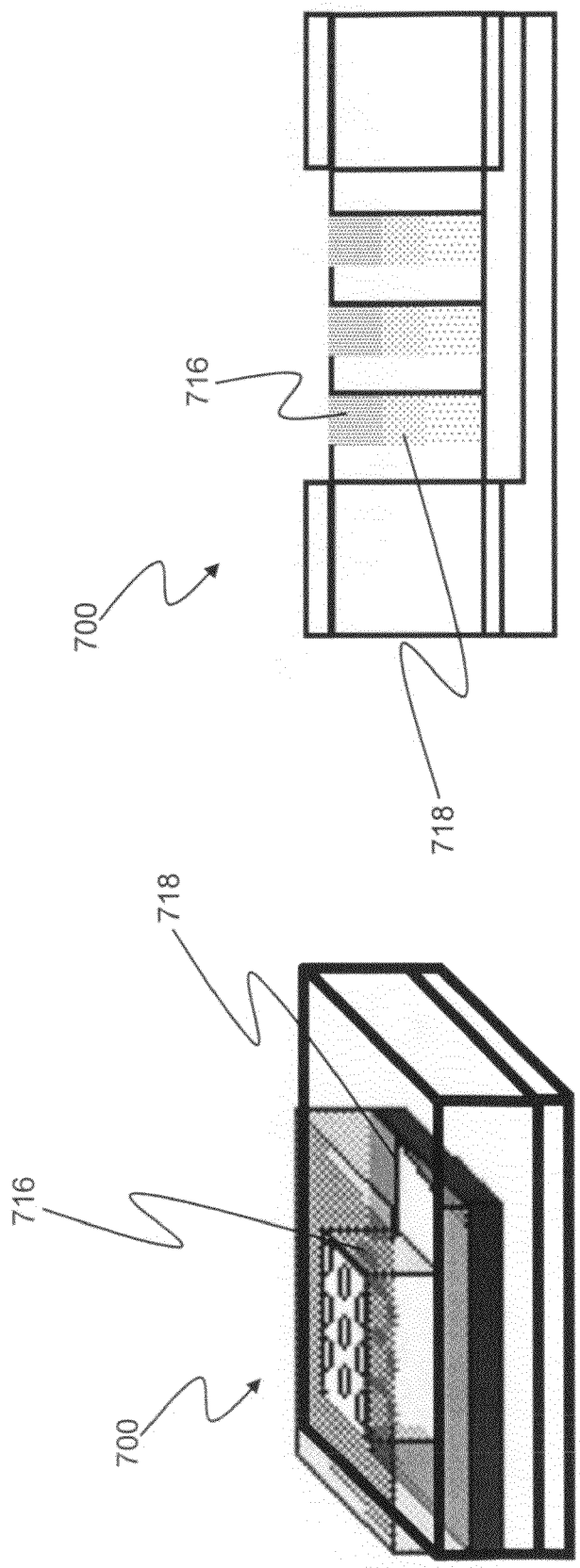

US 8,187,865 B2

NANOWIRE SENSOR, SENSOR ARRAY, AND METHOD FOR MAKING THE SAME

PRIORITY CLAIM

The present application is a Divisional application of U.S. patent application Ser. No. 10/868,755, filed Jun. 14, 2004, entitled "Nanowire sensor, sensor array, and method for making the same," which claims the benefit of priority of U.S. Provisional Patent Application No. 60/477,838, filed Jun. 12, 2003, entitled "Controllable Growth of Individually Addressable Nanowires" and U.S. Provisional Patent Application No. 60/477,841, filed Jun. 12, 2003, entitled "Nanowire Sensing Array for Identification of Chemical Species."

STATEMENT OF GOVERNMENT INTEREST

This invention described herein was made in the performance of work under a NASA contract, and is subject to the provisions of Public Law 96-517 (35 USC 202) in which the Contractor has elected to retain title.

BACKGROUND OF THE INVENTION (1) Technical Field

The present invention relates to a nanowire sensor, sensor array, and method for making the same. More specifically, the present invention relates to a system and method for the fabrication of a conductometric sensor array comprising nano-sized wires.

(2) Description of Related Art

A molecular sensor system offers many advantages over conventional sensor systems. In addition to allowing dense packing of individual sensors, the molecular nature of such a system allows for the detection of very low concentrations of analyte. For sensors where analyte contacts the sensor surface (non-spectroscopic methods), a change in a characteristic of the surface, such as conductivity, capacitance, temperature, resonance frequency, or color, signals the presence of analyte. In conductometric sensors, response is measured as change in conductivity. Conductometric sensors have been made with a variety of sensing materials, including metals, metal oxides, inorganic semiconductors, polymer-carbon composites, and conducting polymers (including organic semiconductors). The mechanism of conductivity change is not the same in all materials, but in all cases, contact with an analyte results in a change in the conductivity of the sensing material. The change is measured as a change in resistance, measured in voltage.

In array based sensing systems, also known as electronic noses for vapor sensing, the sensors have overlapping sensitivities and the response is read as a pattern across the array. Each sensor responds to compounds in a different degree (or manner) from other sensors, resulting in a pattern of responses unique to each compound. Compounds are then identified using pattern-recognition software designed for that purpose and based on laboratory training sets. The magnitude of responses may be used to quantify the analyte with well-characterized sensor sets.

A desirable technique for designing a highly sensitive conductometric sensor is to make the sensing material as thin as possible. Chemical compounds contacting the surface will change the conductivity of the surface, but in a thick film, such a change may be too small to result in a measurable response. Measurement of the responses in these nanosensor systems requires a specifically designed system.

Therefore, a need exists in the art for a conductometric sensor array that requires little power to operate, is easy to manufacture, and whose size will provide for applicability in areas where space is limited.

Additionally, the growth of nanowires is a complex and high-cost procedure, providing little control over the process or result. Present applications allow for the fabrication of nanowires without the ability to either control their growth or their direction.

Therefore, a need exists in the art for the ability to fabricate a nanowire using a controlled-growth process to actively select the dimensions, positions, and alignments of nanowires.

SUMMARY OF THE INVENTION

The present invention relates to a nanowire sensor. The nanowire sensor comprises at least one nanowire formed on a substrate; and a sensor receptor disposed on a surface of the nanowire, forming a receptor-coated nanowire. The nanowire sensor further comprises a sensor sub-unit comprising a plurality of homogeneously receptor-coated nanowires.

In another aspect, the nanowires are formed from a metallic substance, the metallic substance being selected from a group consisting of a metal and a metal oxide compound.

In yet another aspect, the sensor receptor is a formed from a conductive material. The conductive material is a material selective from a group consisting of metal and a conducting polymer. The conducting polymer is selected from a group consisting of polyanilines, polythiophenes, polypyrroles [1,2], conducting polymer-metal oxide, and polymer-metal composites.

Furthermore, the nanowire sensor further comprises a plurality of sensor subunits, the plurality of sensor subunits collectively being a nanowire sensor array. Each sensor subunit in the nanowire sensor array is formed to sense a different stimulus.

In another aspect, the present invention comprises a method for creating a nanowire sensor array. The method comprises acts of fabricating a nanotemplate with nanopores on a substrate for growing nanowires; electrodepositing the nanowires within the nanopores on the nanotemplate in distinct subunits, each subunit consisting of a plurality of nanowires and having two contact sides; and electrodepositing a sensor layer on top of the nanowires to form a nanowire sensor array.

In the act of fabricating a nanotemplate, the nanotemplate comprises a layer of aluminum on a silicon substrate.

Additionally, the act of fabricating a nanotemplate further comprises an act of patterning the layer of aluminum with parylene. In the act patterning the layer of aluminum with parylene, an aluminum thin film is patterned on a silicon substrate using electron-beam lithography to define sensing sub-units.

In another aspect, in the act of fabricating a nanotemplate, a portion of the layer of aluminum is anodized to form nanopores, thereby creating a portion of a nanotemplate of anodized alumina and a portion of a nanotemplate with unanodized aluminum, the anodized portion having the nanopores.

Furthermore, the act of electrodepositing the nanowires within the nanopores on the nanotemplate further comprises acts of depositing an insulating layer on a surface of the portion of the nanotemplate with unanodized aluminum; an act of depositing a patterned metallic contact layer on the nanotemplate; an act of vacuum depositing a thick insulating substrate to support the substrate; and an act of immersing the nanotemplate in a plating bath of a contact material to allow the contact material to grow up through a nanopore and create a nanowire.

Additionally, in the act of electrodepositing the sensor layer, e-beam lithography is used to disconnect individual nanowires and create new, selective interconnects.

Furthermore, in the act of electrodepositing the sensor layer, the sensor surface layer is electrodeposited in selected sub-unit areas to form an electrical nano-contact made of sensor material.

Additionally, the act of electrodepositing the sensor layer further comprises acts of creating an electric field during electrodeposition of the sensor surface layer to guide directional growth of the electrodeposited material; an act of holding select subunits at an appropriate electrical potential to prevent electrodeposition of a particular sensor surface on the select subunits, such that distinct subunits can be created with different sensor surfaces.

In yet another aspect, the method for creating a nanowire further comprises acts of coating a contact layer on at least one contact side of at least one subunit after the act of electrodepositing the sensor layer; and patterning at least one contact side in a selected series-parallel configuration after the act of electrodepositing the sensor layer.

Additionally, in the act of electrodepositing the sensor layer, the sensor layer is a conducting polymer selected from a group consisting of polyanilines, polythiophenes, polypyrroles [1,2], conducting polymer-metal oxide, and polymer-metal composites.

Furthermore, in the act of depositing the patterned metallic contact layer on the nanotemplate, the patterned metallic contact layer is formed from a material selected from a group consisting of gold, platinum, nickel, and palladium.

In another aspect, the method for creating a nanowire sensor array comprises acts of fabricating a nanotemplate with a nanopore on a substrate; electrodepositing a nanowire in the nanopore; electrodepositing a sensor layer in the in the nanopore such that the sensor layer is in contact with the nanowire; electrodepositing a nanowire in the nanopore such that the nanowire is in contact with the sensor layer; and exposing the sensor layer.

In the act of fabricating a nanotemplate with a nanopore on a substrate, the nanopore template comprises a layer of aluminum on a silicon substrate.

In yet another aspect, the act of electrodepositing a sensor layer in the nanopore further comprises an act of depositing a metal nanoelectrode from a liquid electrolyte to create a nanoelectrode base within the nanopore. In the act of depositing a metal nanoelectrode, the metal nanoelectrode is a material selected from a group consisting of gold, platinum, nickel, and palladium.

Additionally, the act of electrodepositing a sensor layer in the nanopore further comprises an act of electrodepositing a sensor layer in selected sub-unit areas.

In another aspect, the act of electrodepositing a sensor layer in the nanopore further comprises acts of creating an electric field during the electrodeposition of the sensor layer to guide directional growth of the electrodeposited material; holding select subunits at an appropriate electrical potential to prevent electrodeposition of a distinct sensor layer on select subunits, such that distinct subunits can be created with different sensor layers; and depositing a second layer of a metal nanoelectrode on the sensor layer to create a contact with the sensor layer.

Additionally, the act of exposing the sensor layer further comprises acts of patterning at least one metal nanoelectrode with E-beam lithography; selectively etching the unanodized aluminum layer using an etchant to expose the sensor layer; and partially removing the anodized alumina layer to maintain the structural integrity of the nanowire sensor array.

In another aspect, the second metal nanoelectrode is a material selected from a group consisting of gold, platinum, nickel, and palladium.

In yet another aspect, the present invention comprises a method for growing nanowires. The method comprises acts of depositing a set of extrinsic layers on a substrate; removing a portion of the extrinsic layers to form an electrolyte channel; and electrochemically growing a nanowire in the electrolyte channel.

The method further comprises an act of preparing the substrate using a standard RCA procedure prior to the act of depositing a set of extrinsic layers on a substrate.

Additionally, the act of depositing a set of extrinsic layers further comprises an act of depositing an insulating layer. The insulating layer is deposited using a technique selected from a group consisting of low-pressure chemical vapor deposition (LPCVD) technique and oxide diffusion.

In another aspect, the act of depositing a set of extrinsic layers further comprises an act of depositing an adhesion layer and a contact layer.

In the act of depositing an adhesion layer and a contact layer, the layers are deposited using a liftoff technique. Additionally, the act of depositing a set of extrinsic layers further comprises an act of depositing a layer of silicon oxide. In the act of depositing a layer of silicon oxide, the layer of silicon oxide is thermally deposited.

Furthermore, the act of removing a portion of the extrinsic layers further comprises an act of selectively opening the deposited layer of silicon oxide to form an electrolyte channel. In the act of selectively opening the deposited layer of silicon oxide, the deposited layer of silicon oxide is selectively opened using e-beam patterning and reactive ion etching.

The act of electrochemically growing a nanowire in an electrolyte channel further comprises acts of placing a drop of electroplating solution on the electrolyte channel; and applying an electric potential between the electrodes.

In the act of applying an electric potential between the electrodes, a nanowire grows from the cathode to the anode through the channel to fill the width and length of the channel.

Additionally, in the act of depositing a set of extrinsic layers on a substrate, the substrate is comprised of silicon.

In yet another aspect, the present invention comprises a method for nanowire fabrication, comprising acts of depositing a set of extrinsic layers on a substrate; and removing a portion of the extrinsic layers to create nanowires on the substrate.

The act of depositing a set of extrinsic layers further comprises acts of depositing a thin substance on the substrate, the thin substance being a substance selected from a group consisting of photoresist and polymethylmethacrylate (PMMA); and depositing a layer of metal on the substrate. In the act of depositing a layer of metal on the substrate, the layer of metal is deposited using a metal sputtering technique. Additionally, layer of metal is a metal selected from a group consisting of platinum and titanium.

The act of removing a portion of the extrinsic layers further comprises acts of etching the layer of metal at normal incidence to produce nanowires along with steps in the substrate; and applying an oxygen plasma to remove the thin substance. Additionally, in the act of etching the layer of metal, the layer of metals is etched using an ion milling technique.

Finally, it can be appreciated by one in the art that the methods described herein may operated manually and/or computer-controlled, and that the instructions for the methods may be incorporated into a computer program product such as an optical or magnetic storage medium.

BRIEF DESCRIPTION OF THE DRAWINGS

The objects, features and advantages of the present invention will be apparent from the following detailed descriptions of the preferred aspects of the invention in conjunction with reference to the following drawings, where:

FIG. 2A is an perspective-view illustration of a sub-unit of the "in-plane" nanowire sensor array shown in FIG. 1;

FIG. 2B is a side-view illustration of a sub-unit of the "in-plane" nanowire sensor array shown in FIG. 1;

DETAILED DESCRIPTION

Figure 1:
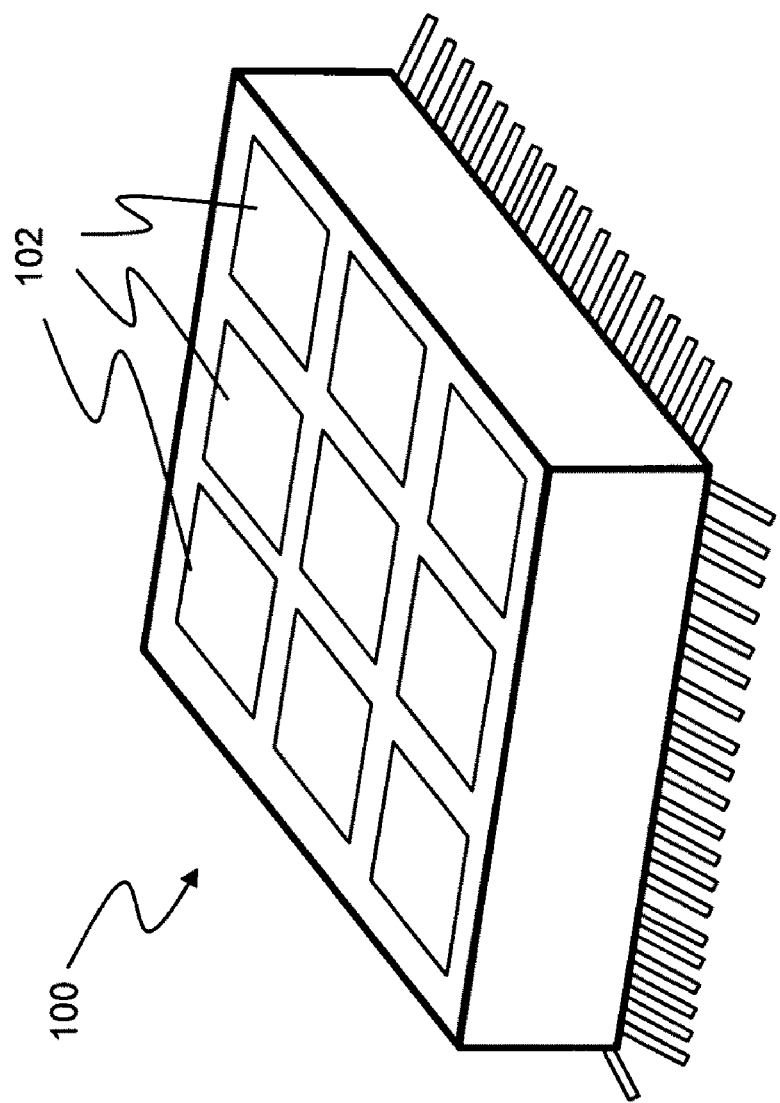
FIG. 1 is an illustration of an "in-plane" nanowire sensor array according to the present invention.

The present invention relates to a nanowire sensor, sensor array, and method for making the same. More specifically, the present invention relates to a system and method for the fabrication of a conductometric sensor array comprising nano-sized wires. The following description, taken in conjunction with the referenced drawings, is presented to enable one of ordinary skill in the art to make and use the invention and to incorporate it in the context of particular applications. Various modifications, as well as a variety of uses in different applications, will be readily apparent to those skilled in the art, and the general principles, defined herein, may be applied to a wide range of aspects. Thus, the present invention is not intended to be limited to the aspects presented, but is to be accorded the widest scope consistent with the principles and novel features disclosed herein. Furthermore, it should be noted that unless explicitly stated otherwise, the figures included herein are illustrated diagrammatically and without any specific scale, as they are provided as qualitative illustrations of the concept of the present invention.

(1) Introduction

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

The description outlined below sets forth a nanowire sensor, sensor array, and method for making the same. A sensor array according to the present invention is fabricated such that portions of the sensor array are individually addressable.

(2) Discussion—Nanowire Sensor and Nanowire Sensor Array

Nanowire sensor arrays made according to the present invention are capable, as a non-limiting example, of detecting chemical compounds in air. This description presents a molecular electronic sensor formed of a nanowire array, as well as a method for making the same. The sensor comprises an ordered array of nanowires arranged in subunits. In a specific embodiment, the sensor comprises an ordered array of nanowires arranged in a set of (e.g., nine) distinct and independent (e.g., one micrometer squared ($\mu m^2$)) subunits. The nanowires support active sensing surfaces and form a connected set of sensors in an ultra-dense system on a substrate (typically silicon). In a specific embodiment, the nanowires are twenty nanometers in diameter spaced 30 nanometers apart, resulting in a density of $10^{11}$ centimeters$^{-2}$ ($cm^{-2}$).

This system of connected nanowires is used to identify and quantify chemical species according to the pattern of response across the array of subunits. Nanowires within a subunit are connected in a series-parallel configuration, to provide both signal amplification and defect tolerance. The active sensing surfaces, or receptors, are conductive materials which form one portion of the series connection for a string of nanowires. Sensor responses are measured as the change in conductivity across the sensing surfaces when analyte molecules contact the surface. Sensor materials are selected to provide sensitivity to the broadest possible suite of analytes; materials are selected based on the target analytes, and, as non-limiting examples, include conducting polymers such as polyanilines, polythiphenes, and polypyrroles, and conducting polymer-metal oxide and polymer-metal composites, such as polyaniline-$TiO_2$. All of these materials respond to the presence of chemical compounds at their surface with a change in conductivity, as the potential energy surfaces of the sensor are altered by sorbed molecules. The conductivity change, measured as resistance, may be as little as one ohm in one megaohm (0.0001%) for parts per billion (ppb) concentrations and lower. The magnitude of change is related to the concentration of analyte molecule. Using, for example, nine distinct sensing materials, it is possible to create a library of response patterns for hundreds of compounds. In an example application, pesticides were utilized as target analytes in testing due to their structural similarity to many chemical warfare agents.

Desirably, the entire sensing system is constructed electrochemically; the template in which the nanowires are grown, the nanowires, and the sensing surfaces (receptors) are fabricated electrochemically. The electrochemical fabrication approach allows a high degree of specificity in the location and chemical identity of a deposit, as well as a high degree of control over its thickness. Electrochemical fabrication methods also enable inexpensive scale-up for producing fully functional systems.

Rapid detection and identification of chemical species at low concentration depends both on sensor thickness and on selection of the sensing material. As just mentioned, use of electrochemical deposition allows a high degree of control over the sensor thickness. This provides the ability to fabricate highly sensitive sensors that may be as thin as a monolayer of sensing material. Use of very thin sensor surfaces also yields rapid response and recovery times. Polymer and metal oxide-based sensors have been shown to be very robust, and can be re-used many times.

The selection of active sensing materials is made by modeling the interaction of target molecules with candidate sensing materials and by modeling the response of the array of subunits to target compounds. For unambiguous identification of compounds, is important to select sensing materials with strong responses to target compounds and which create significantly different patterns across the sensing array. To help select these materials modeling is performed both for rational selection of sensing materials and to simulate array response for use in developing appropriate pattern recognition software. Successful development of a model that can simulate the response of an array will also allow characterization of compounds not on the target list.

The present invention demonstrates the practical use of (metallic) nanowires as an ultra-dense, ordered, interconnected system of electrodes to transduce the response of conductometric sensors (receptors). The active sensing surface can, as a non-limiting example, be made from materials which can be electrochemically deposited, such as conducting polymers. Using an electrochemical approach to deposit sensing material makes it possible to construct sensors which are on the order of a monolayer thick and a few nanometers wide. Such sensors are sensitive to the presence of a few molecules/$nm^2$ (sensitivities on the order of fractional parts-per-billion). The output of these sensors are electrical signals, in a voltage range which can be adapted to match the connection strategy. With a high-definition series-parallel configuration, the electrical signal from the sensors can be amplified while keeping the system defect-tolerant.

In one aspect, a nanowire sensor array known as an "in-plane" model is disclosed, comprising a nanowire sensor system where metallic nanowires make up electrical contacts to active sensing surfaces made from conducting polymers. As depicted in FIG. 1, an exemplary sensor system 100 comprises an array of nine distinct subunits 102, each occupying an area of one micrometer square. The sensor array has a total footprint of 20 square micrometers. Each subunit 102 is a nanowire-sensor system with a unique sensing material and overlapping sensor responses to various analytes (stimulus). The nine subunits of sensors with overlapping sensitivity allow for the identification of compounds for which response patterns are known.

FIG. 2 further illustrates the structure of a subunit in the "in-plane" sensor array. The subunit 102 comprises a nanowire-sensor system, where the nanowires 202 within the subunit 102 are connected in a series-parallel configuration. Additionally, the sensor surface 204 deposited on each nanowire is visible. FIG. 2A depicts the structure of the subunit 102 by illustrating the vertical, series parallel, alignment of the nanowires 202 between the silicate substrate 206, and further showing the deposition of the sensor surface 204 on the nanowire. FIG. 2B is a side-view illustration of a sub-unit of the "in-plane" nanowire sensor array as was shown in FIG. 2A, with corresponding reference numerals.

Active sensing surfaces can be fabricated from conducting polymers or conducting polymer composites sensitive to a broad array of organic and inorganic compounds. The modeling component utilizes molecular modeling of analyte-sensor interaction to select materials and simulate array responses. This model is also useful for deconvolving the response pattern of an unknown compound for characterization of that compound.

Electrochemistry of In-Plane Model

In one aspect, as a non-limiting example, an array of nanowire sensors consisting of nine distinct sensing subunits is fabricated by integrating electrochemical processes with lithographic techniques. These electrochemical processes including anodizing alumina nanotemplate, electrodeposition of nanoelectrodes, and electrodeposition of sensing materials (polymerization of conducting polymer, electroplating of metals, co-deposition). The primary lithographic approach to be used is e-beam (electron) lithography.

Figure 3B:
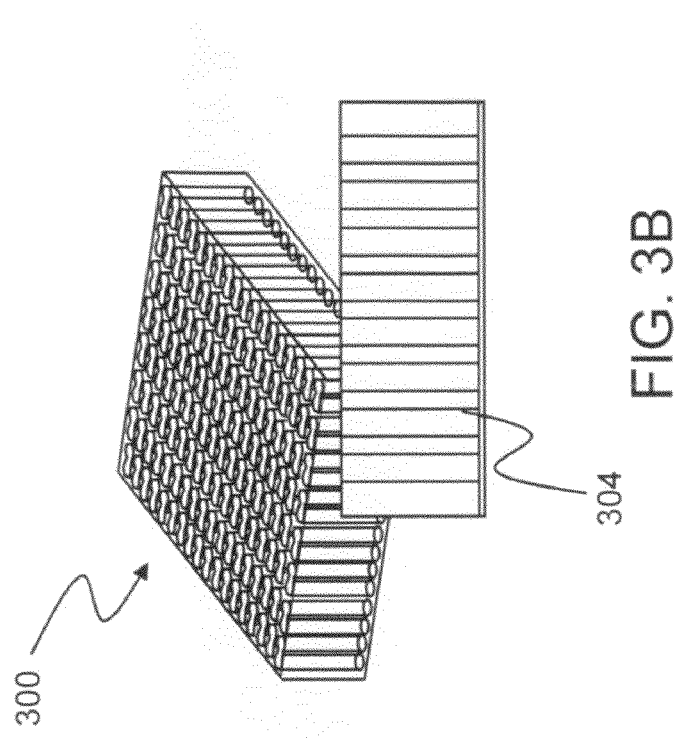
FIGS. 3A-3I are perspective-view illustration of the various acts of a method for making an "in-plane" nanowire sensor array according to the present invention, along with an exploded side-view depicting nanopores in the sensor array.
Figure 3A:
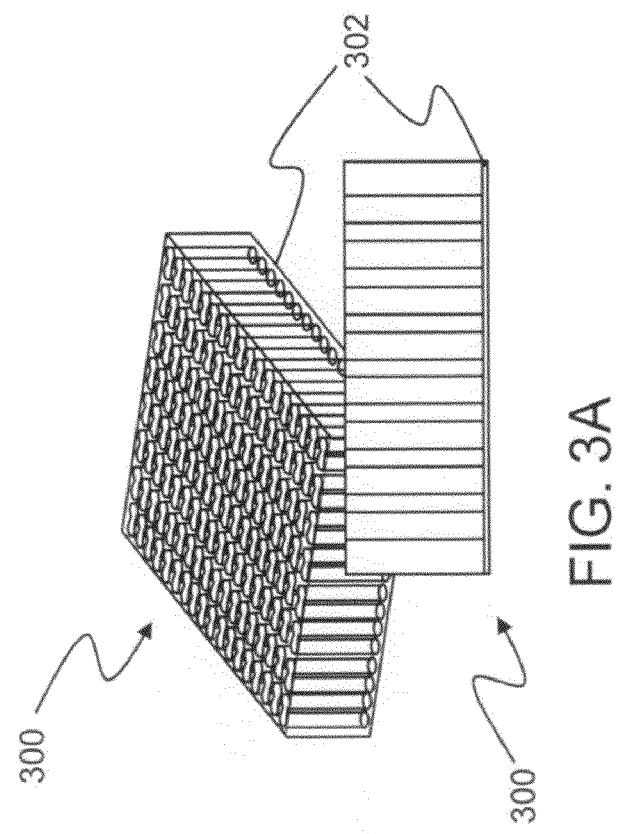

FIG. 3A illustrates the first act in a fabrication scheme in accordance with one aspect of the present invention. Note that throughout the discussion of the device fabrication, non-limiting examples of typical materials used for device fabrication are provided, and that other materials could be used, as known by those of skill in the art. The first act comprises forming an alumina nanotemplate 300 with a layer of sputtered gold 302 on the bottom. A cross section view of the nanotemplate 300 further demonstrates the placement of the layer of sputtered gold 302 on the bottom of the substrate. Anodized alumina is used as a desirable template material. Straight, ordered pores of diameters of 10-200 nanometers can be fabricated with ultra high density pore structures ($10^{10}$ to $10^{12}$ $cm^{-2}$). Unlike track-etched membranes, anodized alumina pores have little or no tilt with respect to the surface, resulting in an isolated, non-connecting pore structure. Anodized alumina is also preferable due to its properties of being electrically insulating ($10^{18}$ ohm-cm), optically transparent over a wide energy band range, chemically stable, and compatible with CMOS processes.

Figure 4:
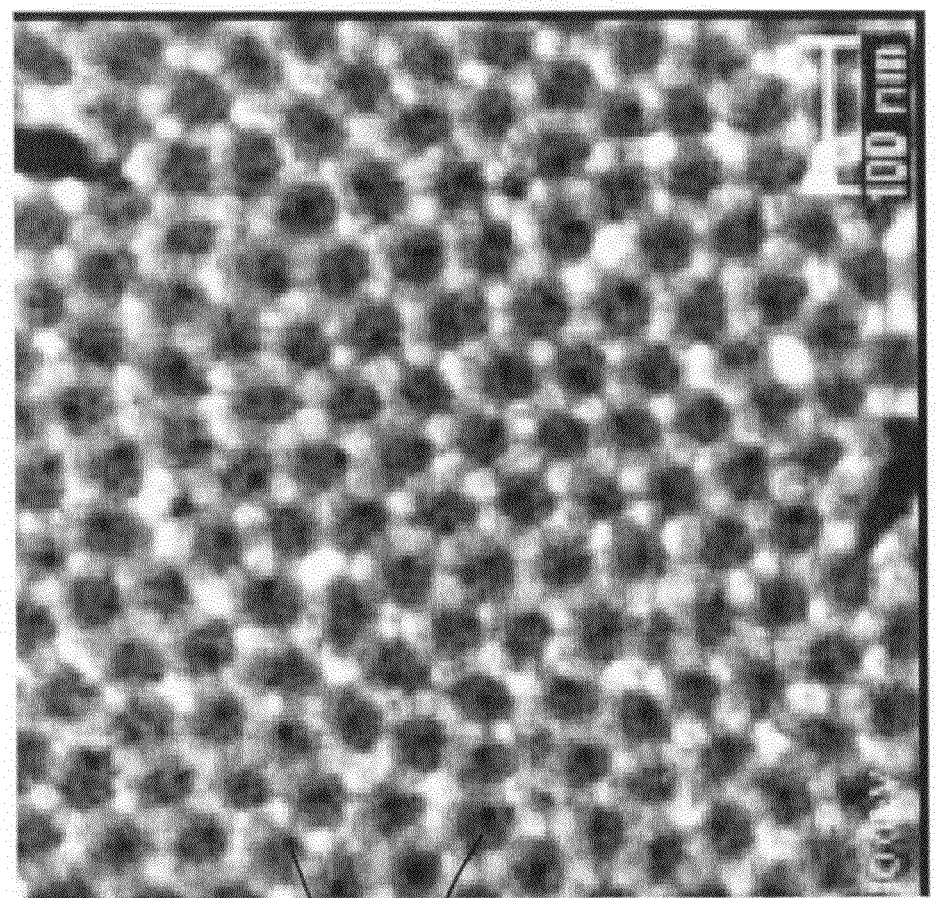
FIG. 4 is a magnified photograph of a set of nanopores (formed as honeycomb structures) on a surface of an nanowire sensor array of the present invention, shown after anodization.

Anodization of aluminum foil or of an aluminum film on silicon oxalic or sulfuric acid results in highly ordered honeycomb structures, as is shown in FIG. 4. After anodization, the resulting nanopores 400 are visible within the alumina template 402. Pore dimensions of 10 nanometers to 200 nanometers can be controlled by adjusting anodizing solution composition and applied current density. Aluminum thin films are preferable because they can be made on a silicon substrate, thus they are integrateable with electronic devices.

In one aspect, prior to anodizing, the aluminum thin film is patterned with parylene using lithography to define sensing sub-units and then anodized to form highly ordered ultra high density alumina nanopores.

Figure 5:
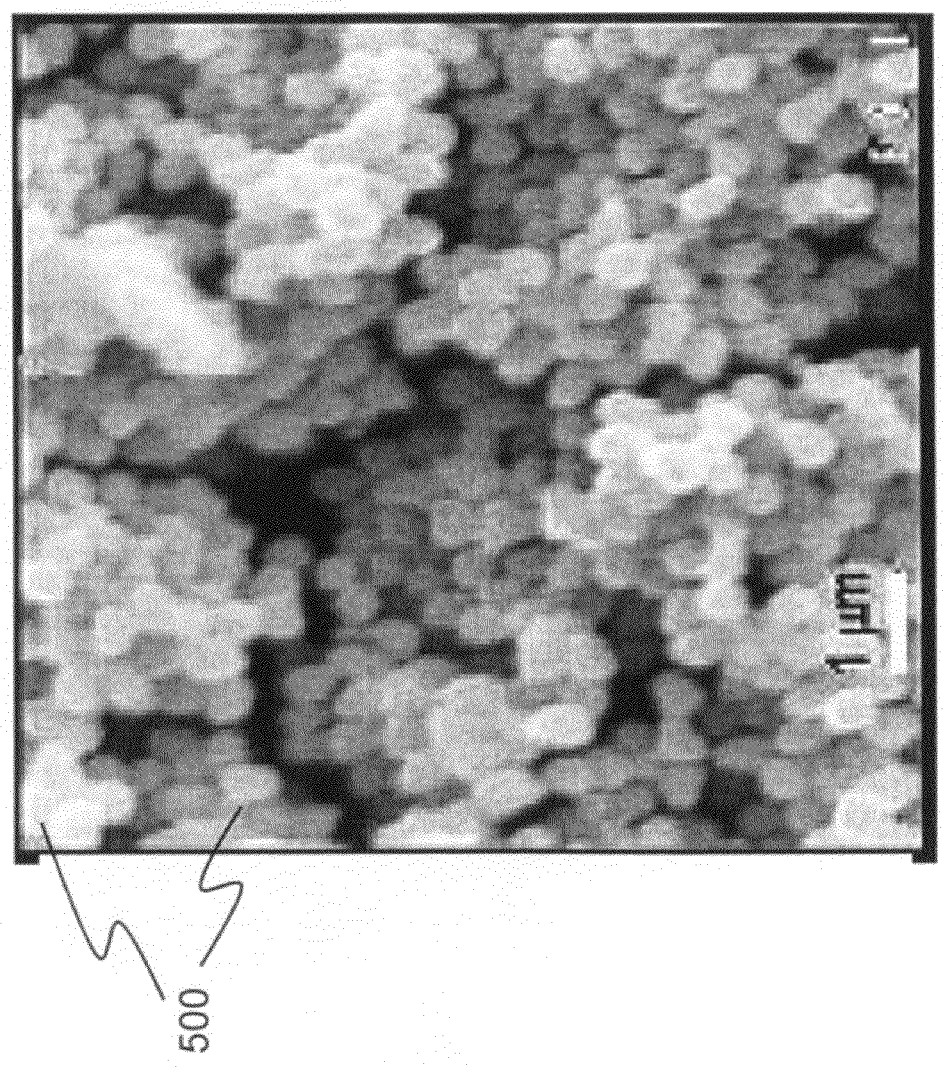
FIG. 5 is a magnified photograph of a set of electrodeposited gold nanowires formed using Whatman Anodisc templates.

The next act is the electrochemical deposition of nanowires, as illustrated in FIG. 3B. Nanoelectrodes are fabricated by filling the nanopores 304 with gold, platinum or other conducting material. Nanowires are formed by electrodeposition. Some of the advantages of electrodeposition include room-temperature and ambient-pressure processing, low energy requirements, fast deposition rates, and inexpensive materials. In one aspect gold and platinum are chosen as materials for the nanoelectrodes for electropolymerization, since they have high chemical stability and good conductivity. Nanowires are grown by immersing the alumina nanotemplates with a gold contact layer into a plating bath. Nanowires grow from the gold contact up through the nanopore. FIG. 5 shows electrodeposited gold nanowires 500 made in commercially available Whatman Anodisc templates. As a non-limiting example, the material used for the nanowires is gold or platinum.

Figure 3D:
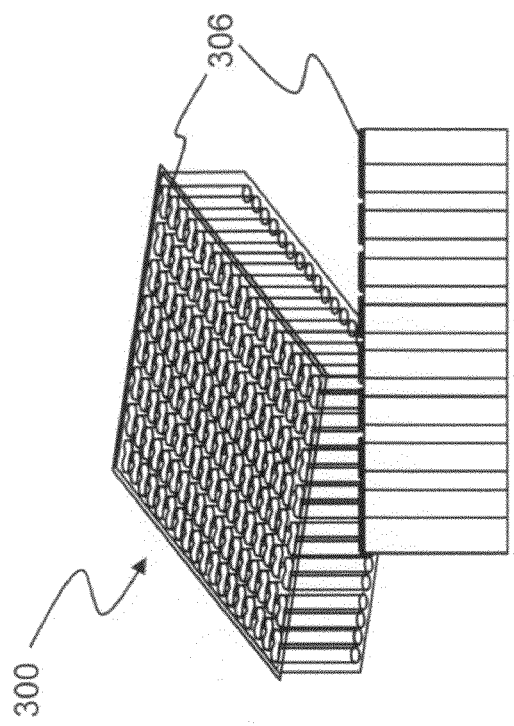
Figure 3C:
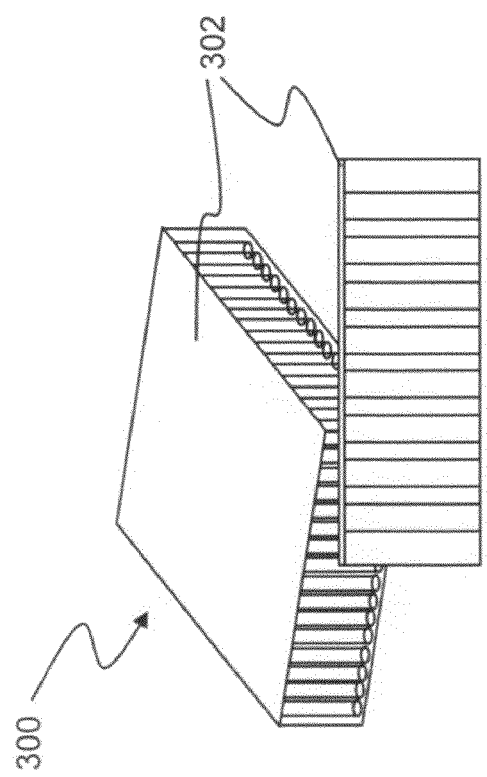

After nanoelectrodes have been electrodeposited, FIG. 3C depicts an act of flipping over the substrate to expose the sputtered gold layer 302. Next, as shown in FIG. 3D, e-beam lithography is used to disconnect individual nanoelectrodes and pattern new, selective, interconnects 306. In one aspect, the silicon substrate is etched through to separate nanoelectrodes. In order to maintain a robust sensing unit, the nanowires should not be released from the template.

Figure 3F:
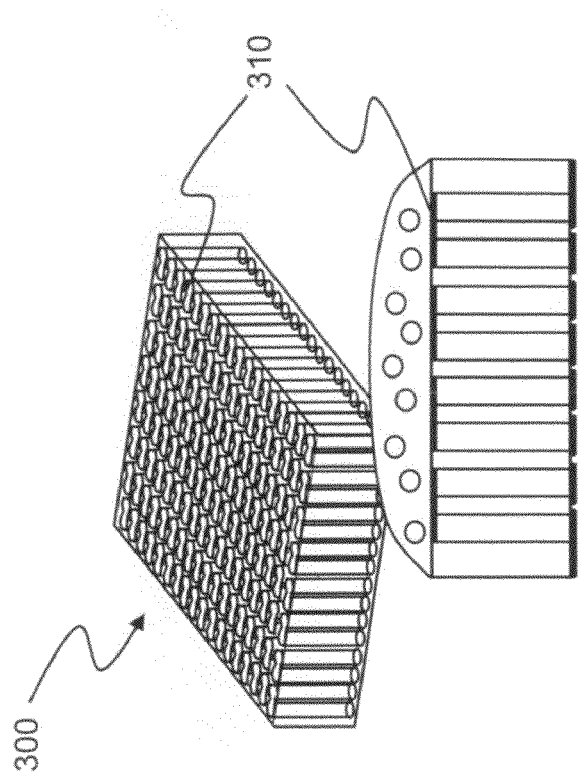
Figure 3E:
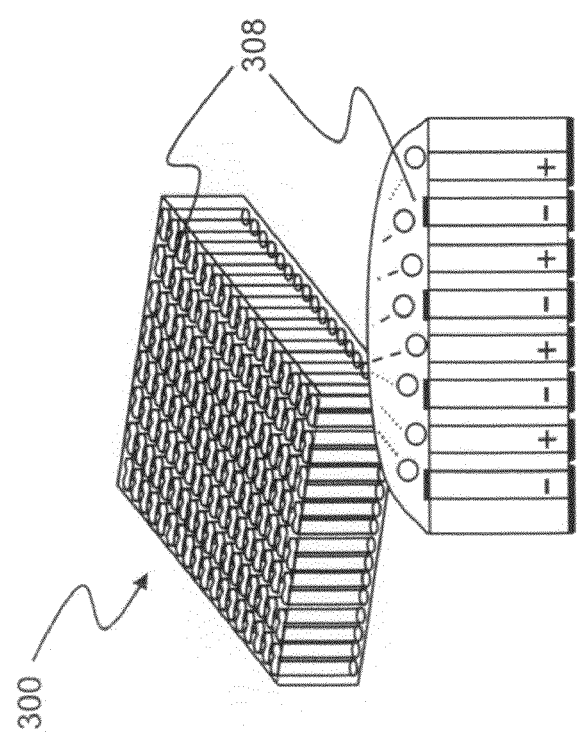

FIG. 3E depicts the act of flipping the substrate again, and depositing the sensing surface 308. In one aspect, sensing surfaces such as conducting polymers are electrodeposited on selected sub-unit areas. An electric field between electrodes guides the growth direction of the electrodeposited material to form an electrical nano-contact made of the sensor material.

Sensing films only grow on the nanoelectrodes which are energized during electrodeposition. Thus, the polymer is not deposited on subunits which are held at an appropriate potential (to protect the surfaces) during the electrodeposition processing. Thus, several distinct subunits, each with a different conducting polymer sensing material, can be created without masking the surface of the substrate. One skilled in the art will appreciate that previously deposited surfaces and bare nanoelectrodes require protection during deposition. Approaches to protection include adjusting the electrolyte composition, adjusting the order in which materials are deposited, holding areas to be protected at open circuit or another potential, and selecting an appropriate material for the nanowires.

Once the sensing surface has been deposited, the electric field is released, allowing the newly deposited sensing surface 310 to fully form a contact with the nanowires, as illustrated in FIG. 3F.

Figure 3H:
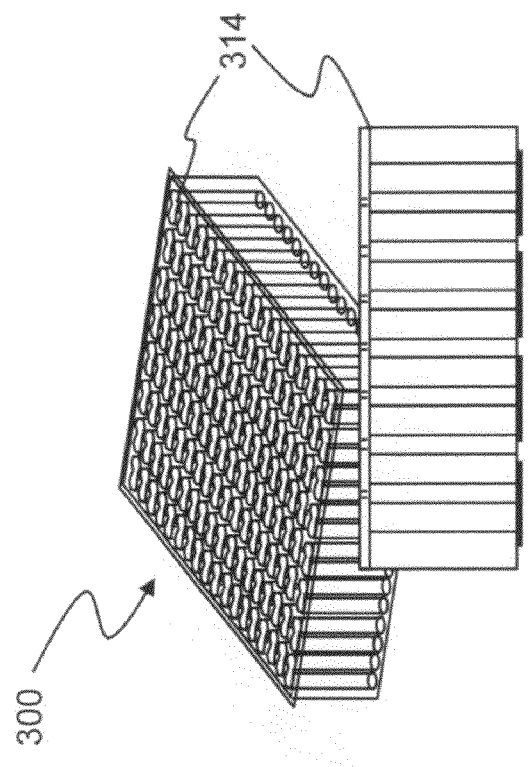
Figure 3G:
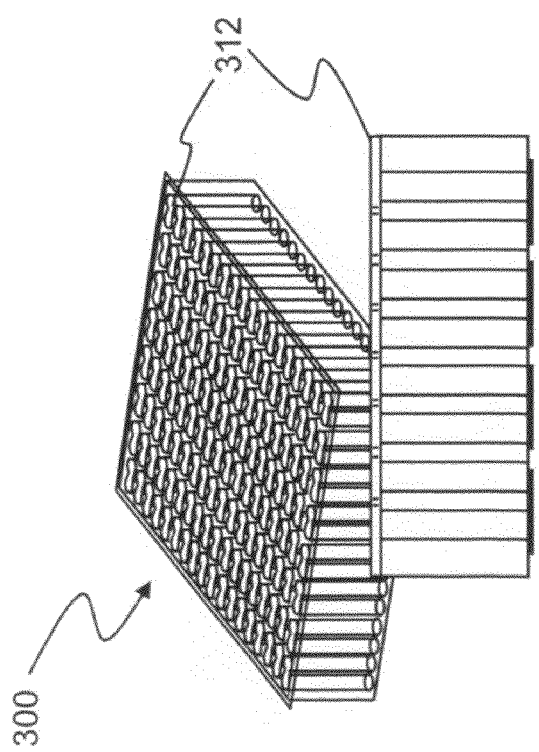
Figure 3I:
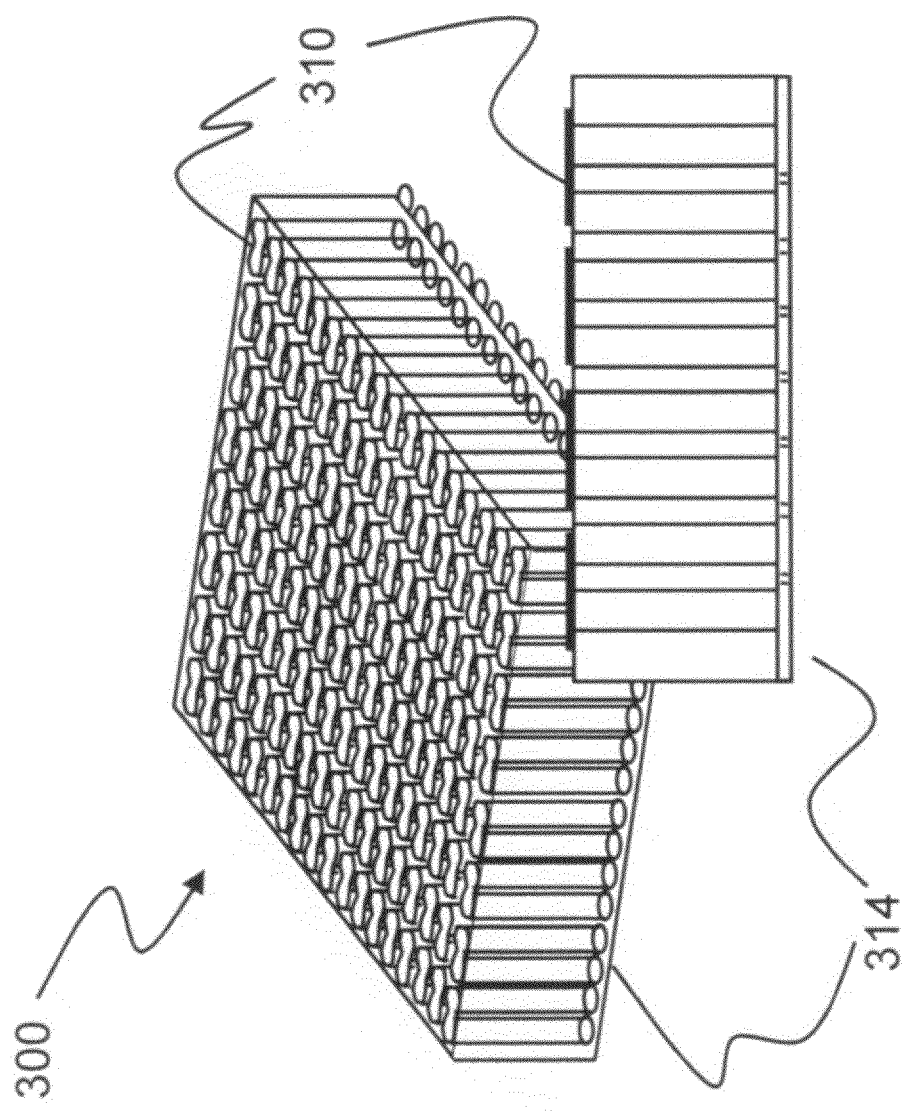

On completion of electodeposition of sensor material, FIG. 3G depicts how the substrate is again flipped and the contact side of the nanowire system is re-sputtered with gold 312. FIG. 3H depicts the use of E-beam lithographic to pattern the contact layer into series-parallel interconnects 314. FIG. 3I depicts the resulting subunit (flipped again), complete with the sensor surface 310, the formed nanowire 316 and contact layer 314 below.

Electrochemistry of Cross-Plane Model

Figure 6:
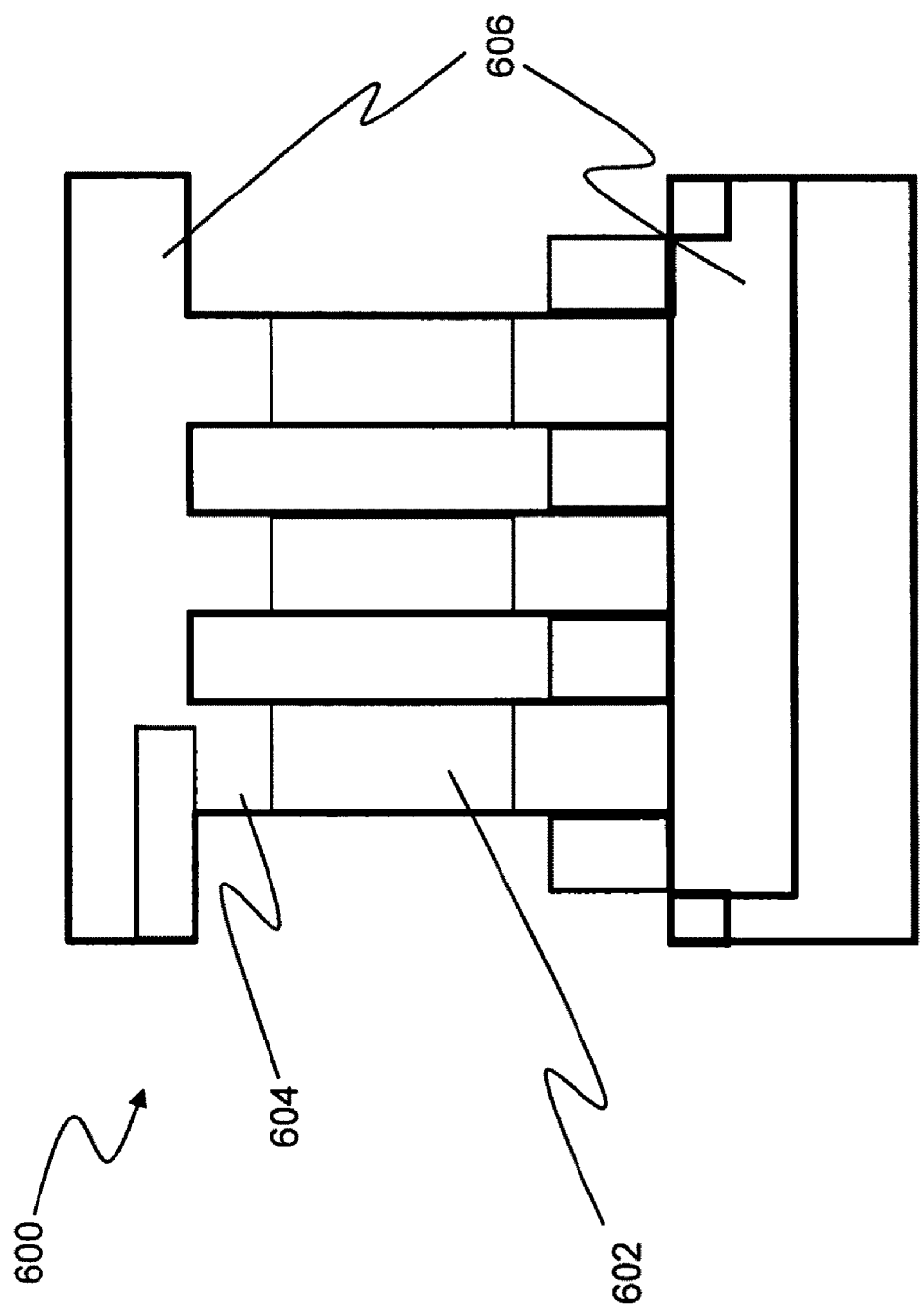
FIG. 6 is an illustration of a "cross-plane" nanowire sensor array according to the present invention.

In another aspect, the present invention provides a "cross-plane" model of the nanowire sensor array, in which conducting polymer sensor layers are grown within the nanopores between two metallic nanowire contacts on the top and bottom. FIG. 6 depicts the nanowire sensor 600 created as a cross-plane model, where the conducting polymer sensor layer 602 lies in the middle of the nanopore 604, with a metallic contact layer 606 on the top and bottom. The nanowires are contacted on top and bottom by pattern metallization in a series-parallel fashion for signal amplification and fault-tolerance. In the cross-plane model, the substrate is etched away to expose the surface of each individual sensor layer. The cross-plane model thus allows each nanowire to be an independent sensor and exposes more surface area of the sensor layer.

Figure 7B:
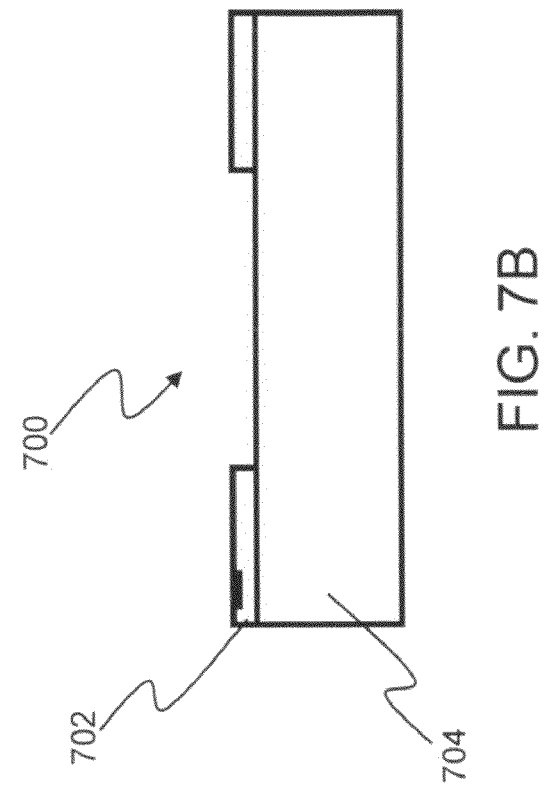
FIGS. 7A-7T are perspective and side-view illustrations of the various acts of a method for making a "cross-plane" nanowire sensor array according to the present invention.
Figure 7A:
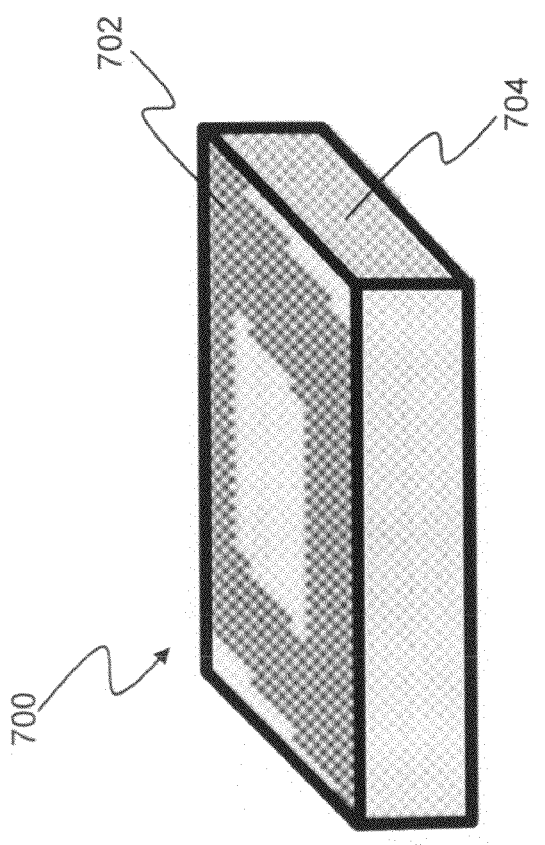
Figure 7D:
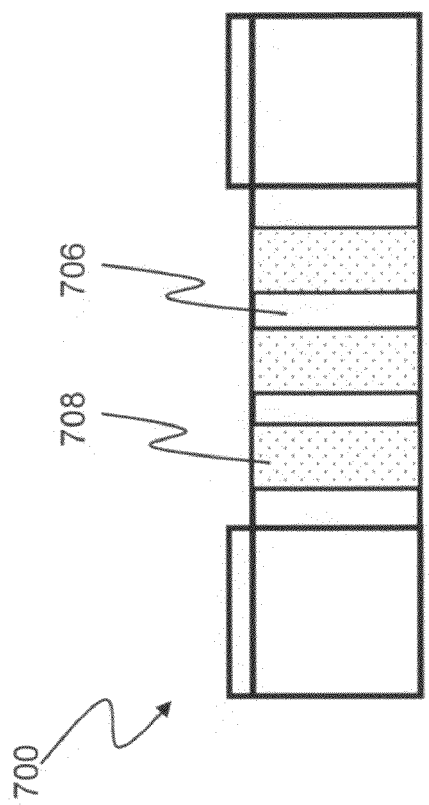
Figure 7C:
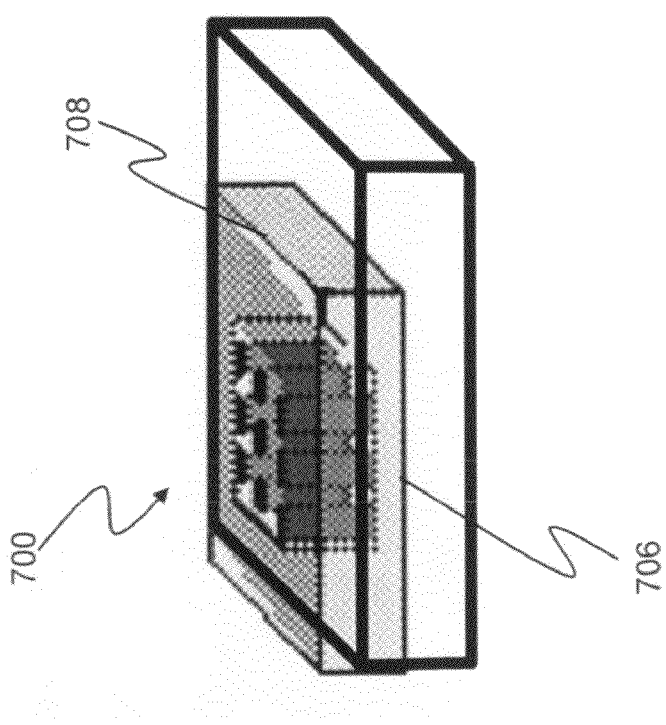
Figures 7E, 7F:
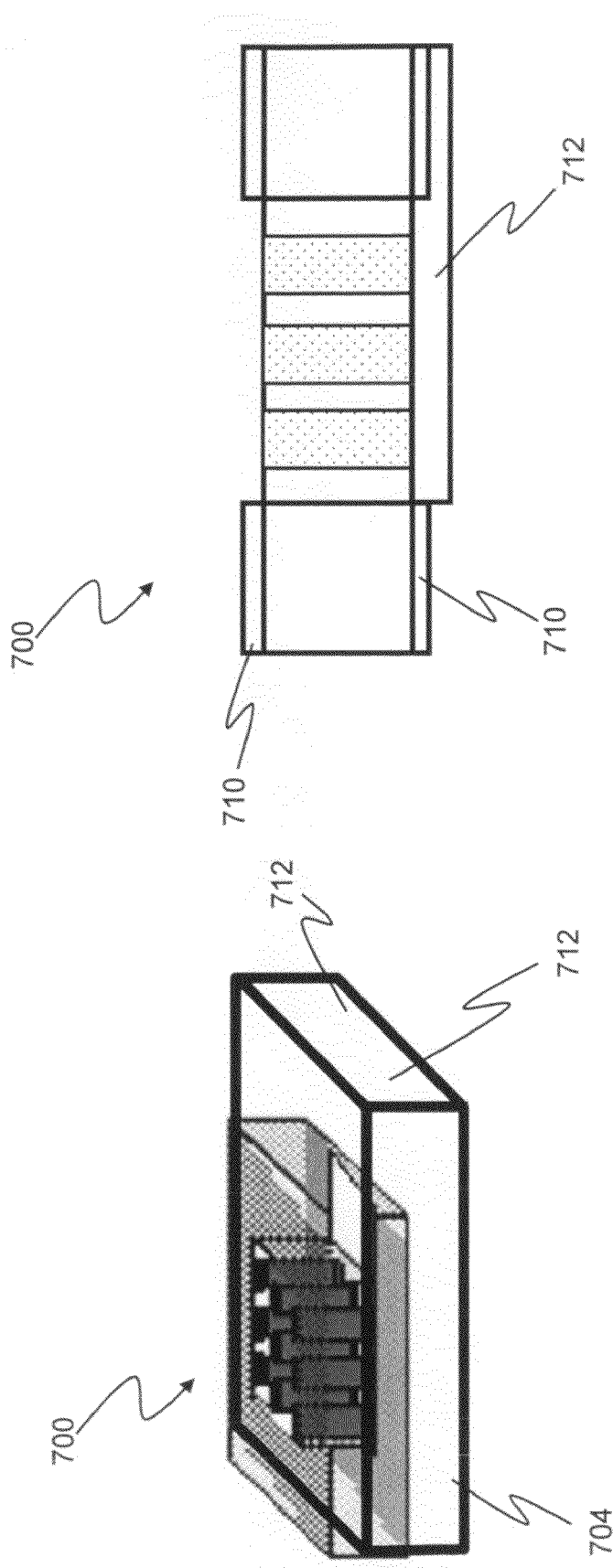
Figure 7H:
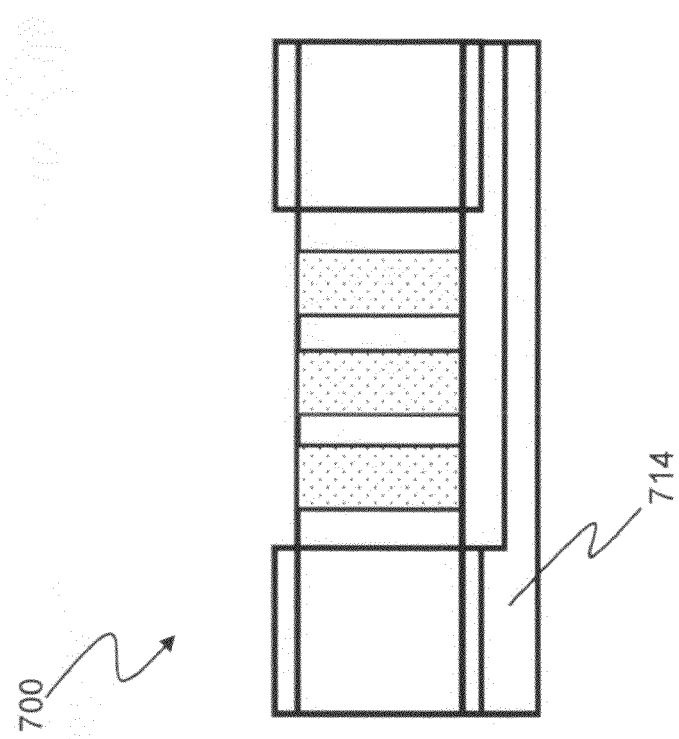
Figure 7G:
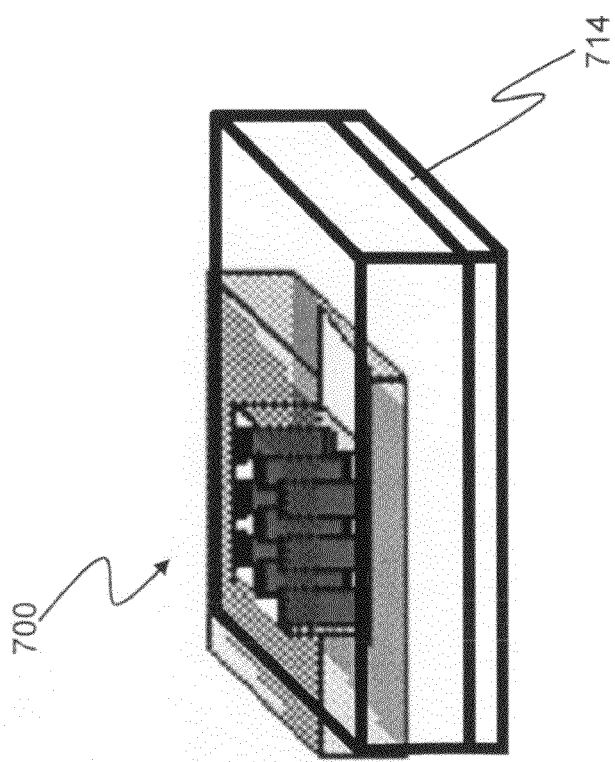
Figure 7J:
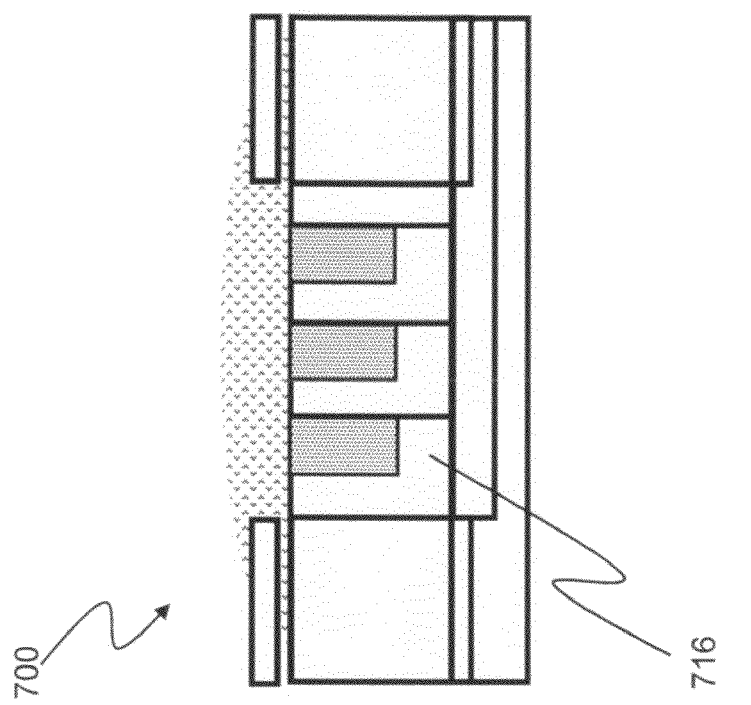
Figure 7I:
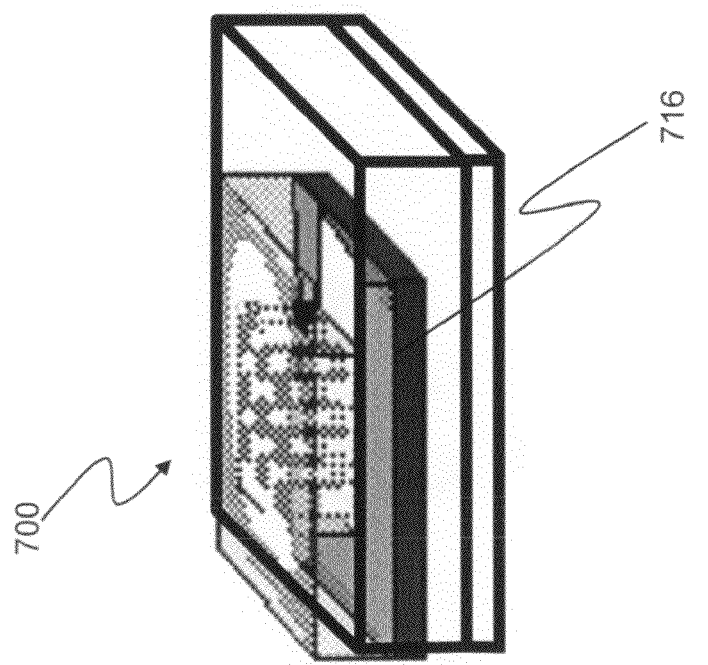
Figure 7L:
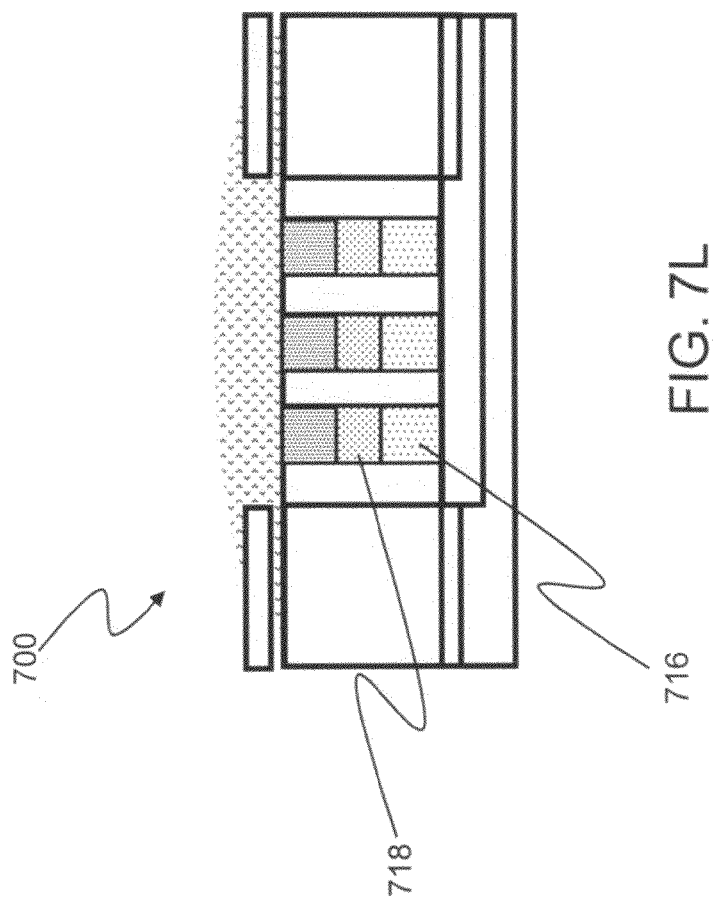
Figure 7K:
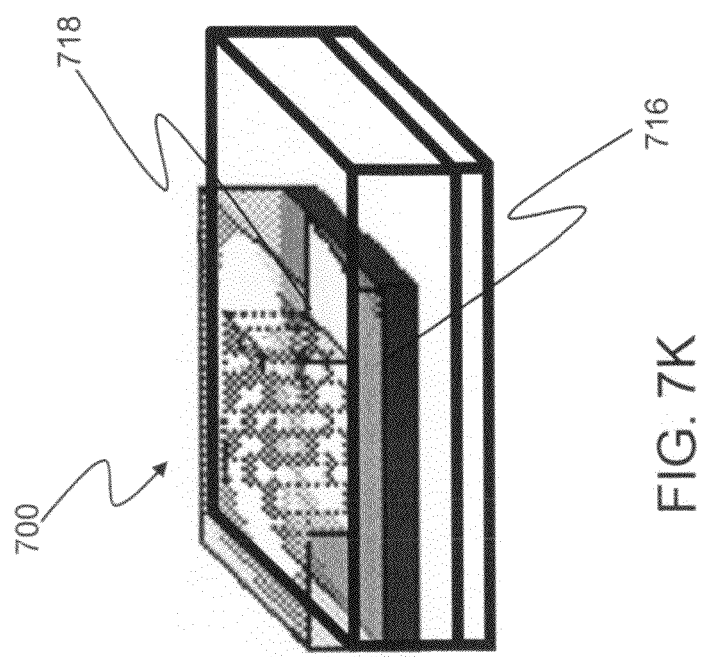
Figure 7P:
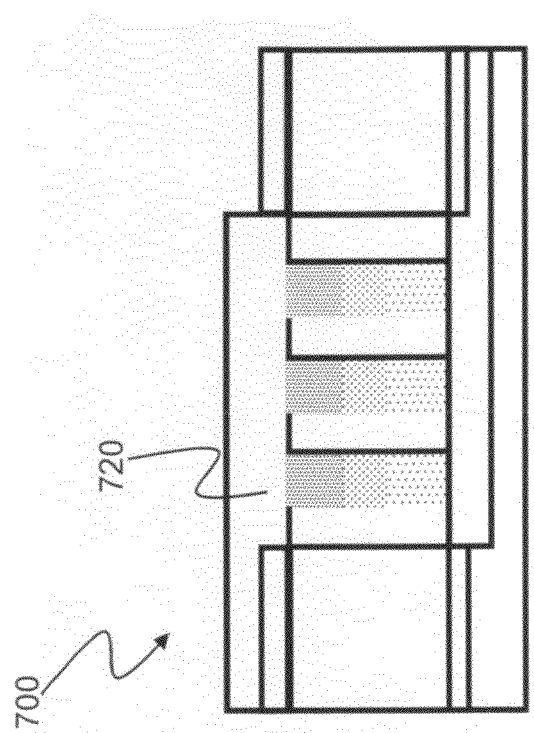
Figure 7O:
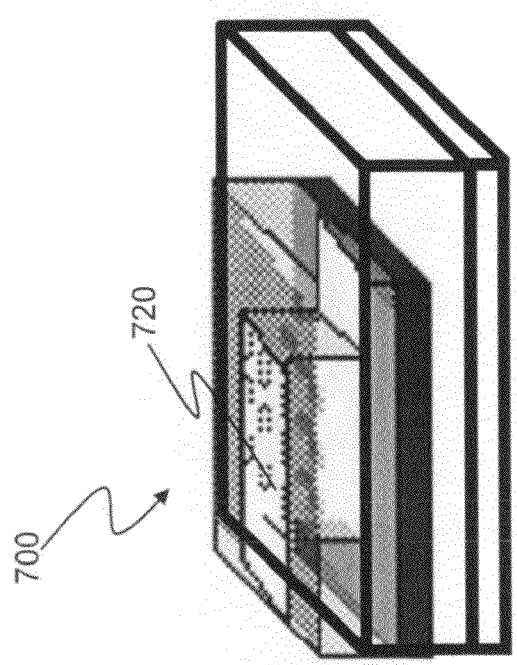
Figure 7R:
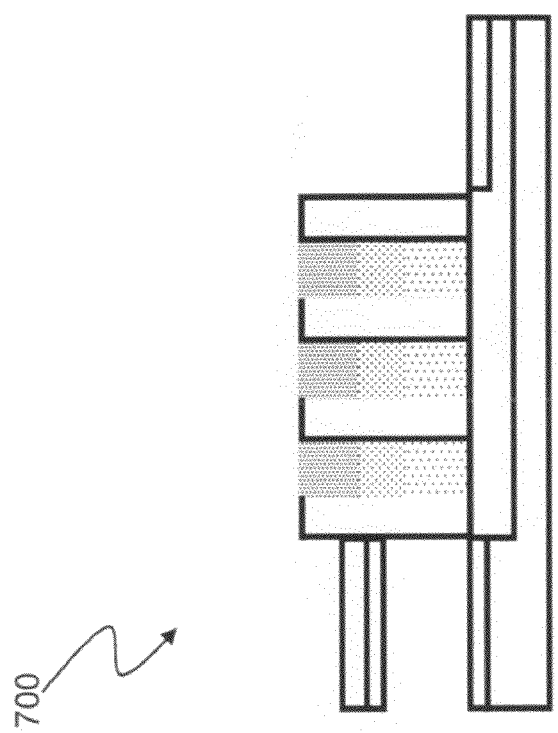
Figure 7Q:
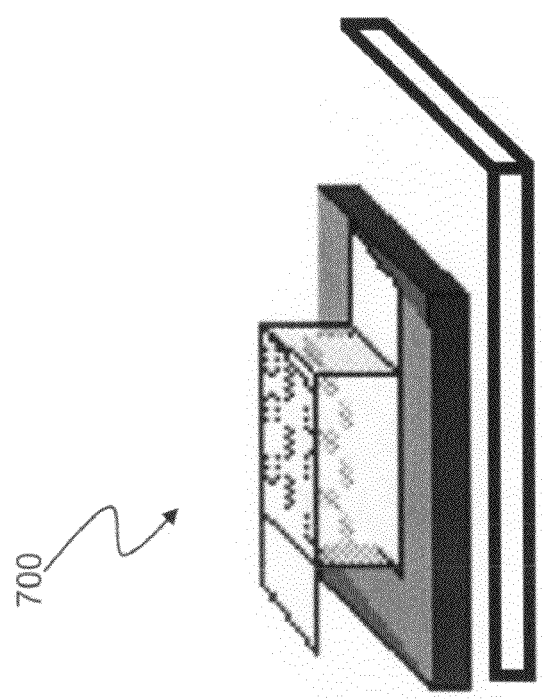
Figure 7T:
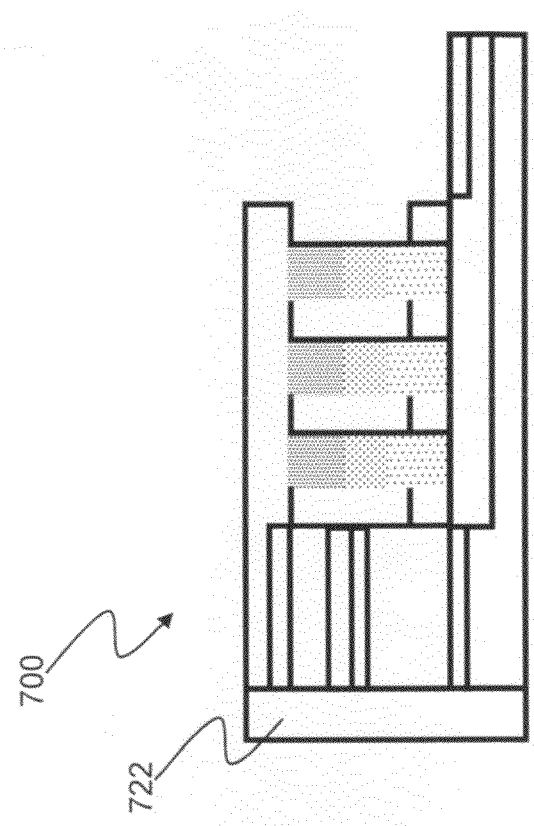

The present invention discloses a method of fabricating the cross-plane model, as illustrated in FIGS. 7A-7T. The first five steps of the cross-plane approach are similar to those of the in-plane approach. In the first step, as illustrated in a perspective view in FIG. 7A and in a side-view in FIG. 7B, a template 700 with an aluminum substrate 704 is patterned and masked using e-Beam lithography, resulting in an exposed anodized aluminum 706 and nanopores 708, as depicted in FIG. 7C and FIG. 7D. Next, as shown in FIG. 7E and FIG. 7F, a patterned metallic contact and interconnect layer with a $Si_3N_4$ insulating layer 710 is deposited between the aluminum layer 704 and metal contact layer 712. The metal contact layer is typically formed of platinum or gold. Next, a thick insulating substrate 714 is vacuum-deposited to support the entire structure, as illustrated in FIG. 7G and FIG. 7H.

Next, as depicted in FIG. 7I and FIG. 7J, the metal nanowire 716 is electrochemically deposited in the nanopores 708 from a solution of liquid electrolyte.

Figure 7S:
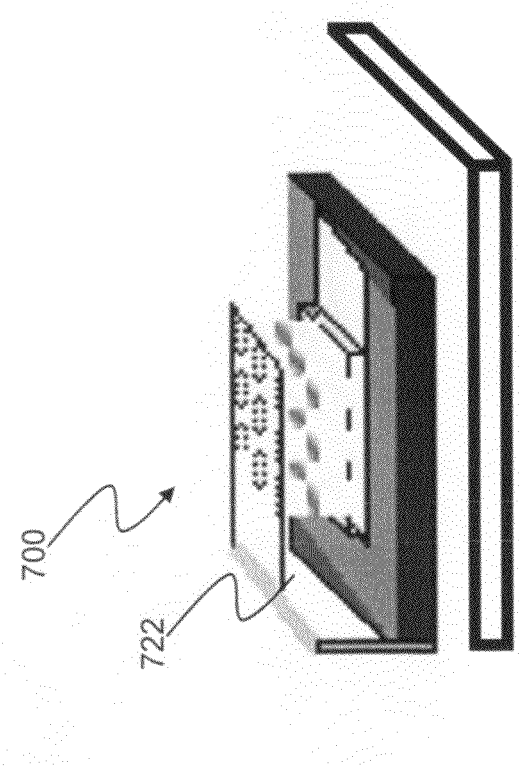

Now, as illustrated in FIG. 7K and FIG. 7L, a conducting polymer sensing layer 718 is deposited on the nanowire 716 using electropolymerization. As shown in FIG. 7M and FIG. 7N, a second nanowire 716 is electrochemically deposited on the polymer sensing layer 718, after which the top nanowire layer 716 is masked and patterned with e-Beam lithography, as depicted in FIGS. 7O and 7P. In the next step, as illustrated by FIGS. 7Q and 7R, the top layer of non-anodized aluminum is selectively etched using $HgCl_2$. Finally, as shown in FIGS. 7S and 7T, the alumina substrate is partially removed to preserve the structural integrity of the now-complete subunit of the nanowire sensor array.

(3) Discussion—Controllable Growth of Individually Addressable Nanowires

In this version of the fabrication method, one nanowire is formed with conventional semiconductor processes including metal deposition, dielectric deposition, e-beam lithography, and electrochemical deposition. The present nanowires are stable under ambient air and aqueous environments. The diameter of the nanowire is as small as 80 nm, with a total length of the wire fabricated in this non-limiting example of 5 micrometers. This method can be used to fabricate individual functioning nanowires and could, for example, be used for nanoelectronic devices and sensors.

A procedure has been developed that allows for single wire growth, with a controlled diameter, from patterned channels by e-beam lithography. In the non-limiting example presented here, the synthesis of palladium nanowires of 80 nm diameter with a length of 5 micrometers is shown using a direct growth method between electrodes. Additionally, the synthesis of polypyrrole nanowires of 500 nm can also be demonstrated. The nanowires are fabricated between electrodes using a room temperature, ambient pressure electro-deposition technique. This electro-deposition technique allows the nanowires to be directly fabricated between the electrodes in a channel, eliminating the current need for post assembly, and thus reducing the cost. Additionally, wide ranges of sensing materials, such as metals, alloys, metal oxides, semiconductors, and conducting polymers can easily be fabricated by alternating electrolyte compositions and deposition conditions. The disclosed method allows for controllable growth of an individually addressable nanowire sensor array with wires having a controlled diameter and length.

Figure 8A:
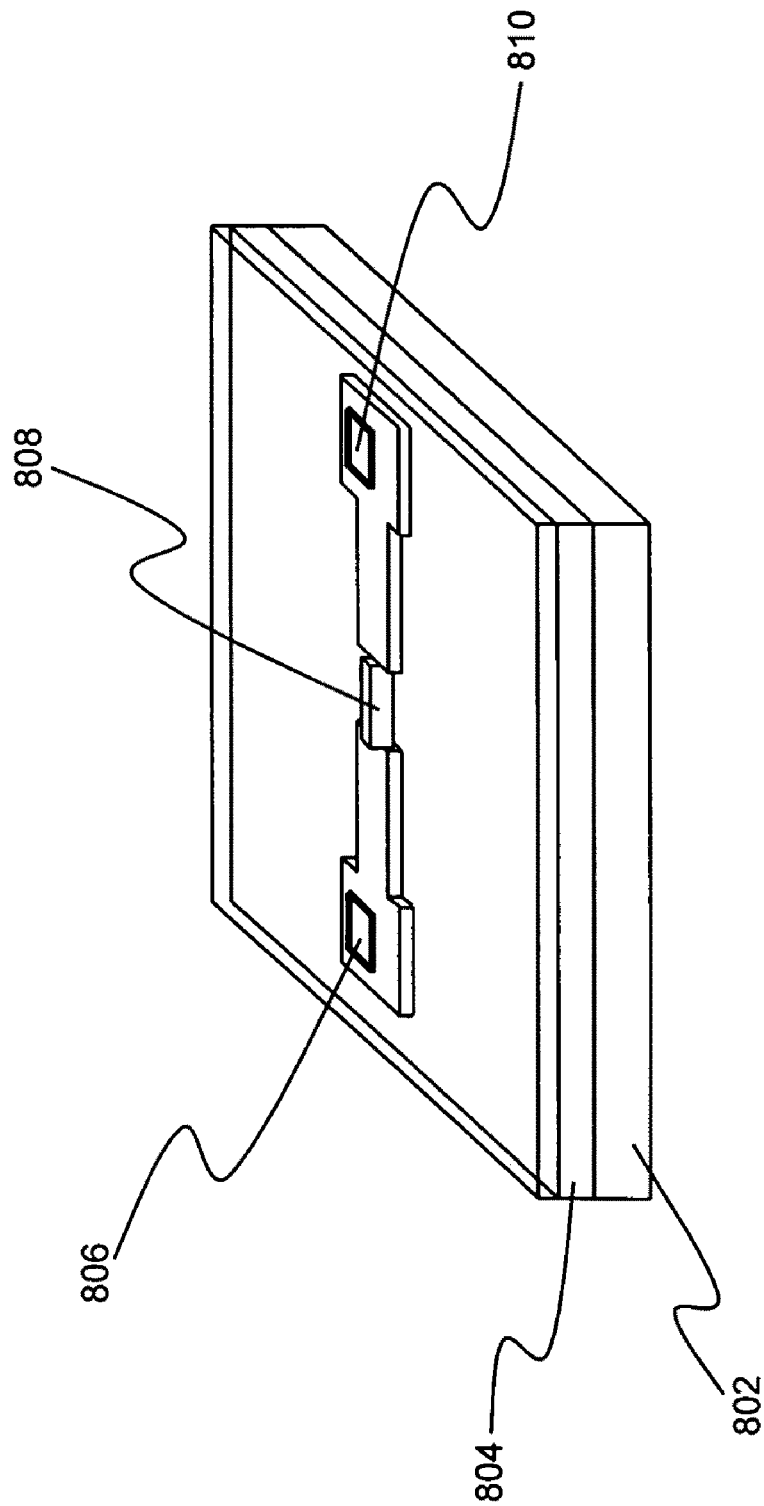
FIGS. 8A and 8B is a perspective-view and side-view illustration of the structure used for the electrochemical wire growth, depicting the electrodeposited layer between electrodes.
Figure 8B:
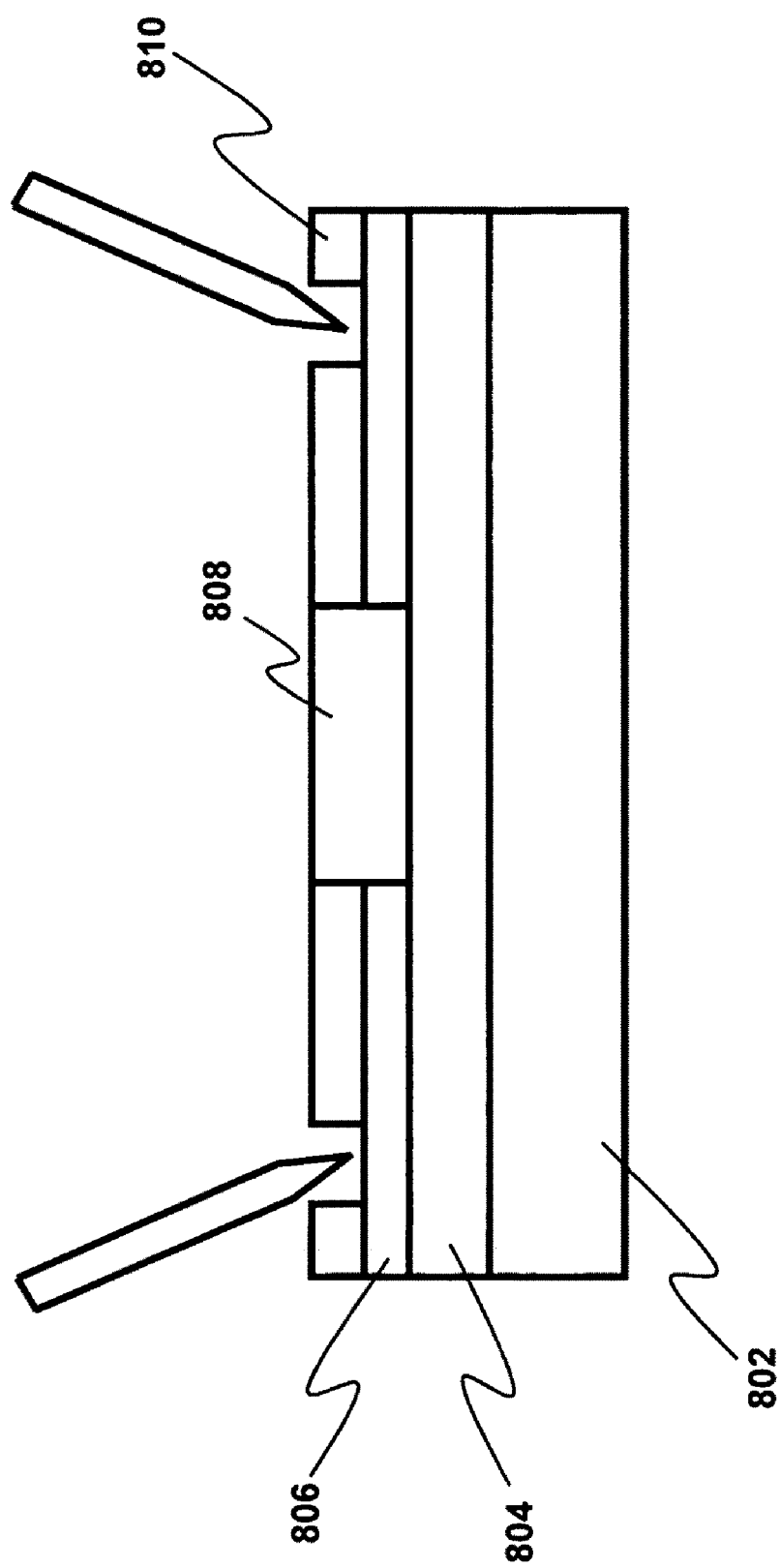

The processes of cleaning, dry etching, low-pressure chemical vapor deposition (LPCVD), lithography, dielectric deposition, e-beam lithography, metallization, and electrochemical deposition are standard semiconductor fabrication techniques. The illustrations in FIG. 8A and FIG. 8B depict a version of the process for fabricating the growth of the nanowire into a sensor array. In a non-limiting example, the silicon substrate 800 is a silicon wafer with (100) orientation and a thickness of 350 micrometers having ±10% variation. The silicon wafers were prepared with standard RCA cleaning (RCA cleaning is named after a cleaning procedure developed by Werner Kern at RCA laboratories). Next, an insulator 802 is deposited on the silicon wafer. In one aspect, the insulator is one micrometer layer of low-stress silicon nitride ($Si_3N_4$), which is deposited using LPCVD or oxide diffusion. Next, a contact layer 804 is formed. As a non-limiting example, the contact layer 804 is a titanium-gold (Ti—Au) metal film deposited using a liftoff technique. Optimally, the thickness of the Ti—Au layer is approximately 3000 Å, which has been experimentally shown to given an desirable electric readout.

Figure 9:
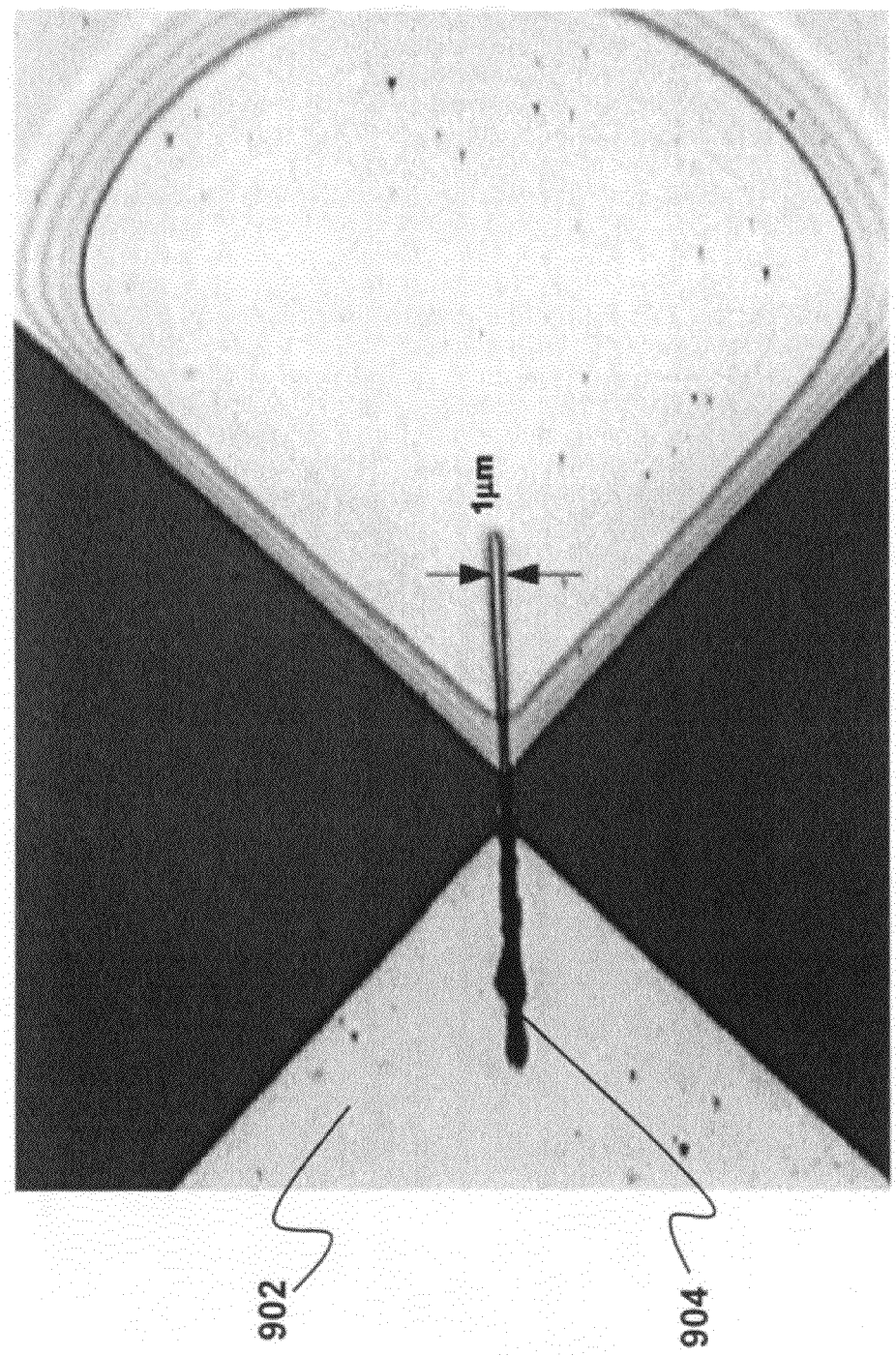
FIG. 9 is a magnified photograph of the electrodeposited nanowires grown between electrodes.

Next, an electrolyte channel 808 is fabricated. In one aspect, a thermal silicon oxide (SiO) deposition technique is chosen to fabricate the electrolyte channel due to the advantage of the room-temperature process. The SiO 806 is deposited on top of the contact layer. The silicon wafer is then patterned. Next, the silicon wafer is e-beam patterned to define the channels with a width of one micron between electrodes, and etched using a reactive-ion etch. Electrochemical deposition is performed by adding a drop of electroplating solution onto a micron channel region on the wafer. As illustrated in FIG. 9, nanowires of palladium (Pd) or polypyrrole 900 are electrodeposited between the electrodes 902 using an aqueous solution of $Pd^{+2}$. The solution is prepared using $Pd(NH_2)_2(NO_2)_2$ (10 g/l), and ammonium sulfamate (100 g/l) adjusted pH 8.0. The electrodeposition based on Pd-salt solution used produces a one-directional and smooth morphology. Directional and smooth morphology provides the ability to produce narrow nanowires.

Figure 10:
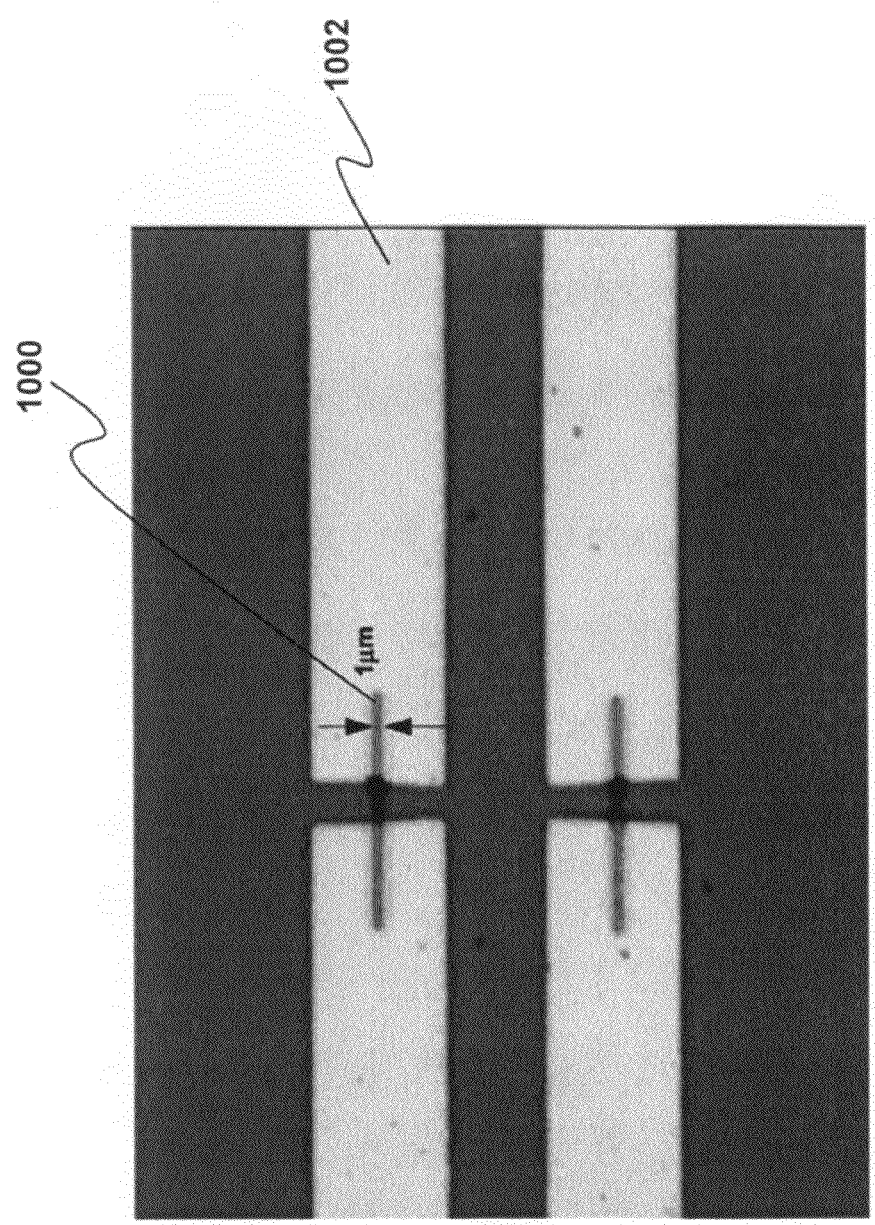
FIG. 10 is a magnified photograph of double nanowires with a common electrode.
Figure 11:
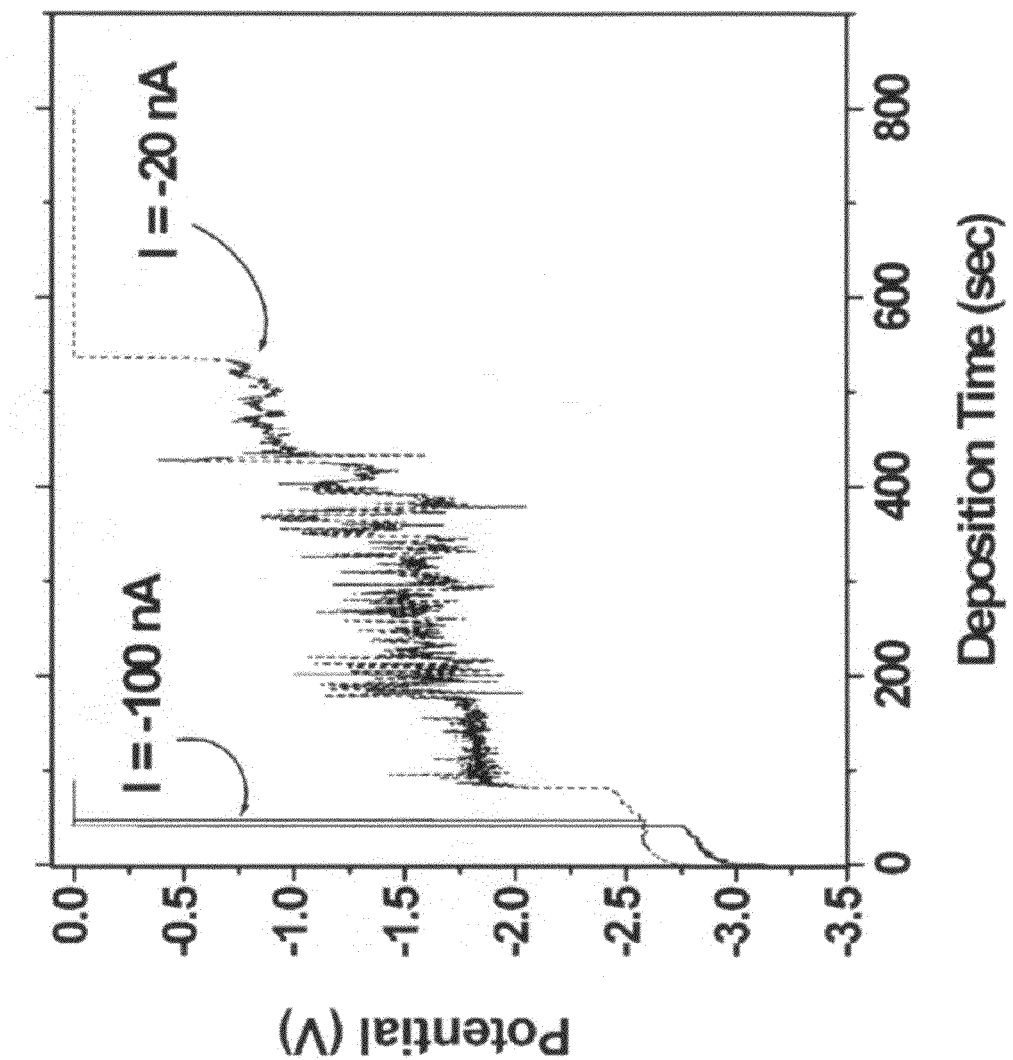
FIG. 11 is a graph representing the measured wire growth potential responses as a function of deposition time.
Figure 12:
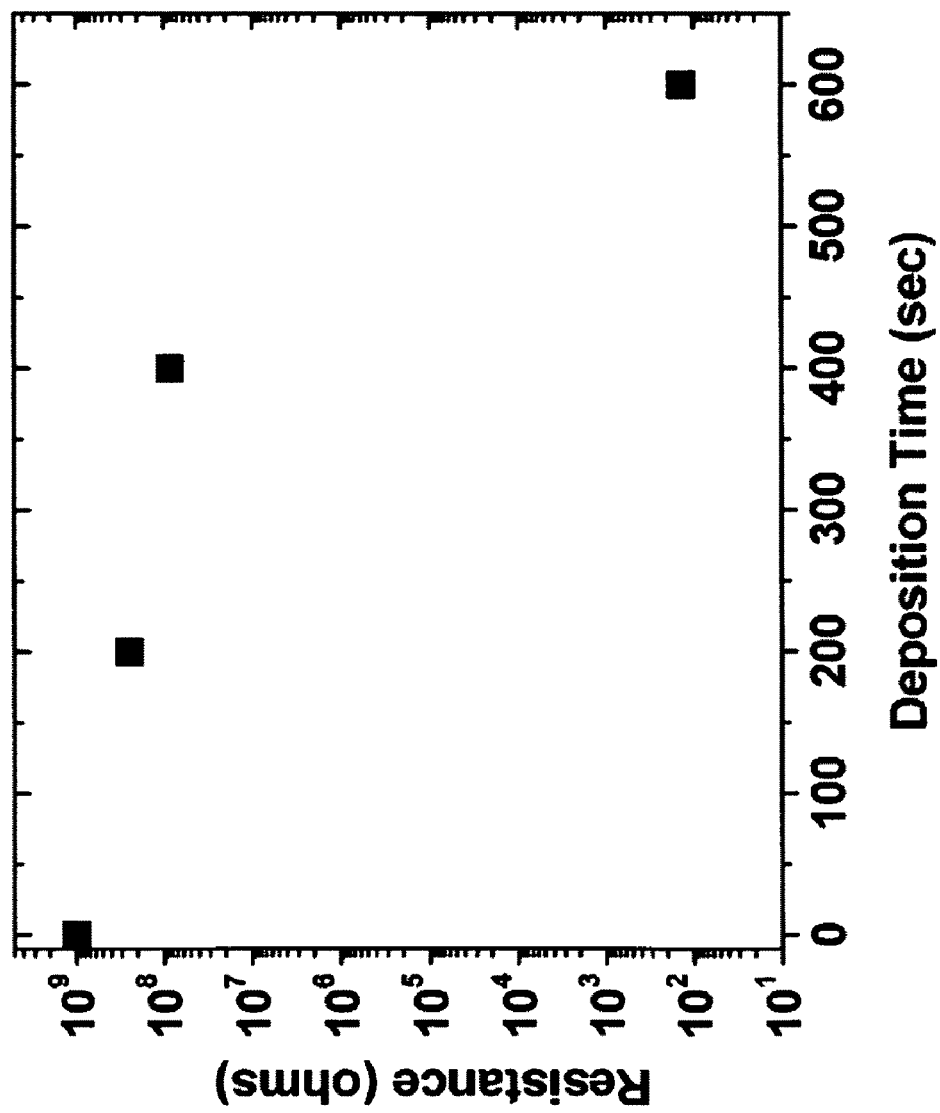
FIG. 12 is a graph representing the resistance change between the anode and cathode as a function of deposition time.

FIG. 10 depicts double Pd micronwires 1000 grown on a single gold (Au) electrode 1002 having a diameter of one micron and a length of five microns.

(4) Discussion—Ion Milling on Steps (IMOS) for Nanowire Fabrication

The disclosed system and method permits the integration of nanowires with multilayer structures. Nanowires have been fabricated with this technique with diameters as small as a few tens of nanometers and lengths as long as millimeters. Ion-milling is used to produce fine lines along with high-aspect-ratio steps of photoresist or polymethylmethacrylate (PMMA).

Space missions, including human exploration, require the development of biochemical sensors to find evidence of life on Mars, for diagnosis and treatment of astronauts' emerging disease, and for environmental control and safety monitoring in the spacecraft. The question of the existence of life on Mars and elsewhere, and diagnosis and treatment of astronauts' emerging disease during their mission are a central focus of many of the space missions planned by NASA and other space exploration agencies.

Nanowire-based sensors are ideal candidates to sense amino acids and early molecular signatures of astronauts' emerging disease because nanowire-based sensors exhibit a fast response (<<milliseconds) with a substantially higher sensitivity, <10 µM, lower power, nanowatts, with a smaller volume than existing sensors.

Semiconductor and metal nanowires and carbon nanotubes have been the subject of intense interest as sensors and electronic devices for high density circuits. The techniques used to fabricate these devices have included using an atomic force microscope to manipulate individual carbon nanotubes onto pre-patterned electrodes, random dispersion of suspended carbon nanotubes in solution onto a substrate with pre-patterned electrodes. While these methods have been adequate for demonstrating the operational characteristics of individual devices, the methods have intrinsic drawbacks of low throughput and limited controllability, which make them unattractive for scaling up for circuits. Attempts to improve fabrication controllability have included applying an electric field for post-growth alignment metal nanowire arrays on a selectively etched superlattice template followed by manual transfer to the desired substrate, and fludic alignment of semiconductor nanowires on a substrate followed by e-beam lithography to form contacts. Additionally, device fabrication with controllability, reproducibility, and yield suitable for large scale circuits remains a significant challenge.

The disclosed system and method enables fabrication of nanowire sensors with controlled dimensions, positions, and alignments. The disclosed system and method involves sputtering and ion milling on the sidewall of photoresist or (PPMA) steps without using e-beam lithography. This disclosed system and method enables fabrication of multi-layer nanowires with the capability of simultaneously detecting multiple chemical species.

Figure 13A:
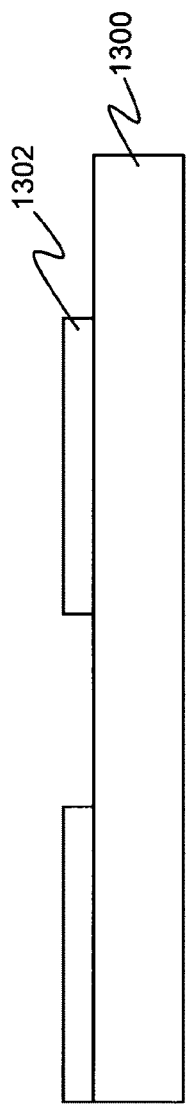
FIGS. 13A-13E are side-view illustrations of the various acts of a method for fabricating a nanowire using ion milling on steps (IMOS)
Figure 13B:
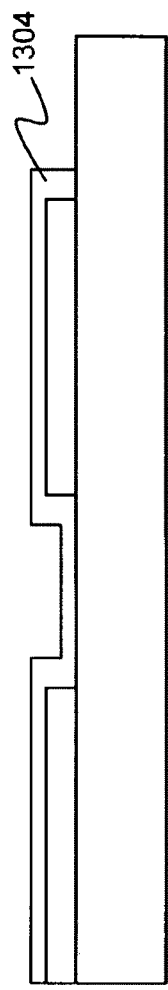
Figure 13C:
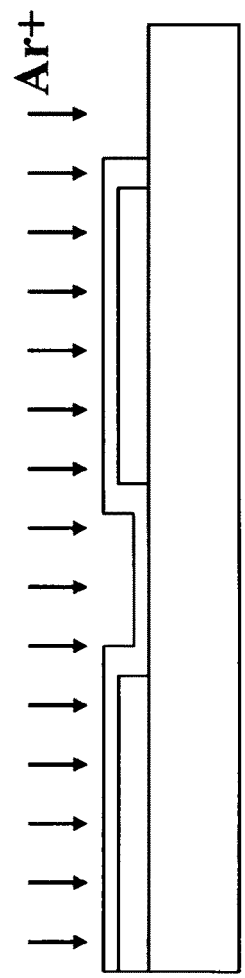
Figure 13D:
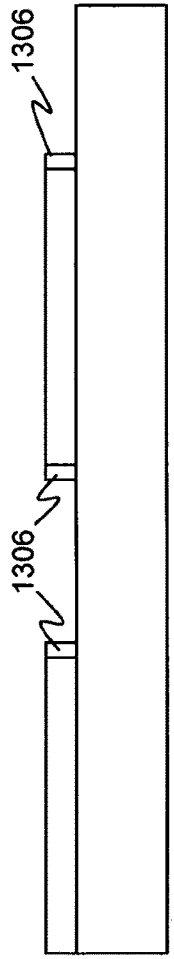
Figure 13E:
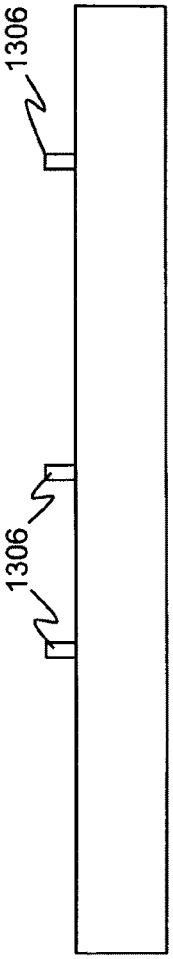
Figure 14:
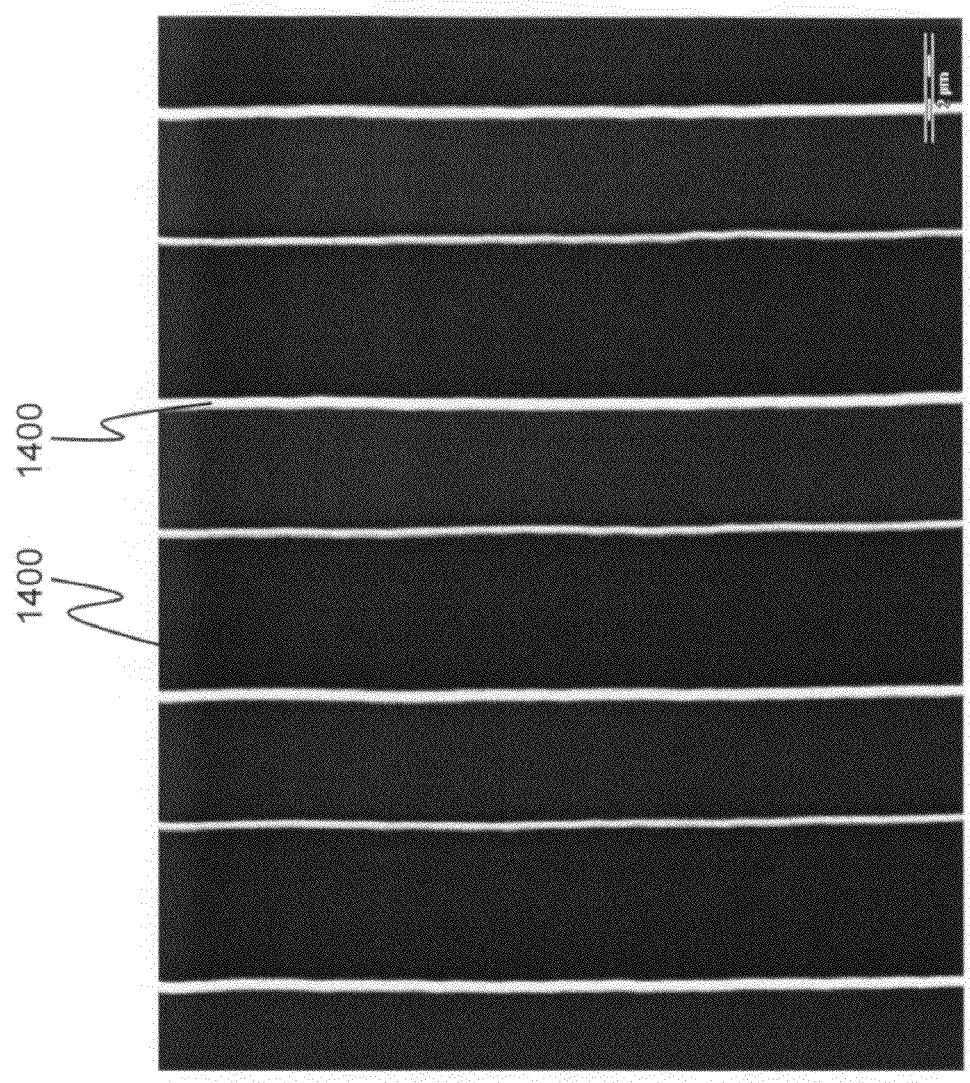
FIG. 14 is a magnified photograph of the resulting nanowires fabricated using IMOS.

FIG. 13A-13E shows, schematically, the processes to fabricate nanowires as disclosed. A silicon substrate 1300 is coated with a thin photoresist (or PPMA) 1302 up to 500 nanometers thick. Then metals 1304, preferably platinum or titanium, are deposited using sputtering up to 200 nanometers thick. Ion milling is then performed, and the metals are etched at normal incidence to produce nanowires 1304 along with steps in the substrate. Finally, an oxygen plasma is used to clean the photoresist 1302 off of the surface. FIG. 13E depicts a cross-sectional view of the final structure of the fabricated nanowire 1304. FIG. 14 shows SEM pictures of nanowires 1400 fabricated using IMOS method demonstrating 100 nanometer and 200 nanometer thicknesses of metal nanowires.

Below is a list of references pertaining to this invention. These references may be found in appendix A attached herewith. All of these references are incorporated herein in their entirety.

"Nanowire Sensing Array for Identification of Chemical Species," DARPA BAA 03-12, Applications of Molecular Electronics Technology (MoleApps).

"Electrochemically Grown Wires for Individually Addressable Sensor Arrays," Nano Letters, 2004, Vol. 4, No. 3, pp. 419-422.

New Technology Transmittal, National Aeronautics and Space Administration.

"Nanowire Sensing Array for Identification of Chemical Species," Broad Agency Announcement 03-12 Application of Molecular Electronics Technology, Proposal Abstract.

What is claimed is:

1. A method for creating a nanowire sensor array, the method comprising acts of:

fabricating a nanotemplate with nanopores on a substrate for growing nanowires;

electrodepositing the nanowires within the nanopores on the nanotemplate in distinct subunits, each subunit consisting of a plurality of nanowires and having two contact sides; and electrodepositing a sensor layer on top of the nanowires to form a nanowire sensor array;

wherein in the act of fabricating a nanotemplate, the nanotemplate comprises a layer of aluminum on a silicon substrate;

wherein the act of fabricating a nanotemplate further comprises an act of patterning the layer of aluminum with parylene;

wherein in the act patterning the layer of aluminum with parylene, an aluminum thin film is patterned on a silicon substrate using electron-beam lithography to define sensing sub-units.

2. A method for creating a nanowire sensor array as set forth in claim 1, wherein in the act of fabricating a nanotemplate, a portion of the layer of aluminum is anodized to form nanopores, thereby creating a portion of a nanotemplate of anodized alumina and a portion of a nanotemplate with unanodized aluminum, the anodized portion having the nanopores.

3. A method for creating a nanowire sensor array as set forth in claim 2, wherein the act of electrodepositing the nanowires within the nanopores on the nanotemplate further comprises an act of depositing an insulating layer on a surface of the portion of the nanotemplate with unanodized aluminum.

4. A method for creating a nanowire sensor array as set forth in claim 3, wherein the act of electrodepositing the nanowires within the nanopores on the nanotemplate further comprises an act of depositing a patterned metallic contact layer on the nanotemplate.

5. A method for creating a nanowire sensor array as set forth in claim 4, wherein the act of electrodepositing the nanowires within the nanopores on the nanotemplate, further comprises an act of vacuum depositing a thick insulating substrate to support the substrate.

6. A method for creating a nanowire sensor array as set forth in claim 5, wherein the act of electrodepositing the nanowires within the nanopores on the nanotemplate, further comprises an act of immersing the nanotemplate in a plating bath of a contact material to allow the contact material to grow up through a nanopore and create a nanowire.

7. A method for creating a nanowire sensor array as set forth in claim 6, wherein in the act of electrodepositing the sensor layer, e-beam lithography is used to disconnect individual nanowires and create new, selective interconnects.

8. A method for creating a nanowire sensor array as set forth in claim 7, wherein in the act of electrodepositing the sensor layer, the sensor surface layer is electrodeposited in selected sub-unit areas to form an electrical nano-contact made of sensor material.

9. A method for creating a nanowire sensor array as set forth in claim 8, wherein the act of electrodepositing the sensor layer, further comprises an act of creating an electric field during electrodeposition of the sensor surface layer to guide directional growth of the electrodeposited material.

10. A method for creating a nanowire sensor array as set forth in claim 9, wherein the act of electrodepositing the sensor layer, further comprises an act of holding select sub-units at an appropriate electrical potential to prevent electrodeposition of a particular sensor surface on the select sub-units, such that distinct subunits can be created with different sensor surfaces.

11. A method for creating a nanowire sensor array as set forth in claim 10, further comprising an act of coating a contact layer on at least one contact side of at least one subunit after the act of electrodepositing the sensor layer.

12. A method for creating a nanowire sensor array as set forth in claim 11, further comprising an act of patterning at least one contact side in a selected series-parallel configuration after the act of electrodepositing the sensor layer.

13. A method for creating a nanowire sensor array as set forth in claim 12, wherein in the act of electrodepositing the sensor layer, the sensor layer is a conducting polymer selected from a group consisting of polyanilines, polythiophenes, polypyrroles [1,2], conducting polymer-metal oxide, and polymer-metal composites.

14. A method for creating a nanowire sensor array as set forth in claim 13, wherein in the act of depositing the patterned metallic contact layer on the nanotemplate, the patterned metallic contact layer is formed from a material selected from a group consisting of gold, platinum, nickel, and palladium.

* * * * *